United States Patent
Bartee et al.

(10) Patent No.: US 12,059,335 B2
(45) Date of Patent: Aug. 13, 2024

(54) DEVICE FOR GUIDED BONE AND TISSUE REGENERATION

(71) Applicant: Osteogenics Biomedical, Inc., Lubbock, TX (US)

(72) Inventors: Barry K. Bartee, Lubbock, TX (US); Chad M. Bartee, Lubbock, TX (US); Istvan Urban, Culver City, CA (US)

(*) Notice: Subject to any disclaimer, the term of this patent is extended or adjusted under 35 U.S.C. 154(b) by 561 days.

(21) Appl. No.: 16/999,057

(22) Filed: Aug. 20, 2020

(65) Prior Publication Data

US 2020/0375716 A1    Dec. 3, 2020

Related U.S. Application Data

(63) Continuation of application No. 15/465,571, filed on Mar. 21, 2017, now abandoned, which is a
(Continued)

(51) Int. Cl.
*A61F 2/28* (2006.01)
*A61B 17/06* (2006.01)
(Continued)

(52) U.S. Cl.
CPC ...... *A61F 2/0063* (2013.01); *A61B 17/06166* (2013.01); *A61B 17/08* (2013.01);
(Continued)

(58) Field of Classification Search
CPC ........... A61F 2/2846; A61F 2250/0052; A61C 8/0006
See application file for complete search history.

(56) References Cited

U.S. PATENT DOCUMENTS

| 3,678,933 A | 7/1972 | Moore et al. |
| 3,699,958 A | 10/1972 | Szucs |

(Continued)

FOREIGN PATENT DOCUMENTS

| DE | 102012024206 A1 * | 6/2014 | ........... A61F 2/2803 |
| DE | 102012024206 A1 | 6/2014 | |
| EP | 0574091 A2 | 12/1993 | |

OTHER PUBLICATIONS

Buser et al. "Regeneration and Enlargement of Jaw Bone Using Guided Tissue Regeneration", Clin. Oral Impl. Res., vol. 1:22-32 (1990).

(Continued)

*Primary Examiner* — Megan Y Wolf
(74) *Attorney, Agent, or Firm* — LOZA & LOZA, LLP; Anthony G. Smyth

(57) ABSTRACT

This disclosure describes a membrane configured to guide bone and tissue regeneration for a bone defect. The membrane may comprise a first layer, a second layer, one or more perforations, a binder, and/or other components. The first layer of the membrane may be configured to contact bone. The first layer may include pores configured to promote ingrowth of bone regenerating cells into the first layer. In some implementations, the first layer may be a continuous sheet of microporous material without large perforations. The second layer may be configured to substantially prevent fibrous connective tissue from growing into the bone defect. The second layer may comprise a relatively dense structure. The second layer may be fixedly coupled to the first layer. In some implementations, the perforations may comprise co-axial through-holes having common dimensions through the first layer and the second layer. The perforations may be configured to enhance ossification.

14 Claims, 16 Drawing Sheets

Related U.S. Application Data continuation-in-part of application No. 14/313,685, filed on Jun. 24, 2014, now abandoned.

(51) Int. Cl.

| | | |
|---|---|---|
| *A61B 17/08* | (2006.01) | |
| *A61B 17/84* | (2006.01) | |
| *A61B 17/86* | (2006.01) | |
| *A61C 8/02* | (2006.01) | |
| *A61F 2/00* | (2006.01) | |
| *A61L 27/18* | (2006.01) | |
| *A61L 27/56* | (2006.01) | |
| *A61L 31/02* | (2006.01) | |

(52) U.S. Cl.
CPC ............ *A61B 17/84* (2013.01); *A61B 17/846* (2013.01); *A61B 17/86* (2013.01); *A61C 8/0006* (2013.01); *A61F 2/28* (2013.01); *A61F 2/2846* (2013.01); *A61L 27/18* (2013.01); *A61L 27/56* (2013.01); *A61L 31/022* (2013.01); *A61F 2002/0068* (2013.01); *A61F 2002/2835* (2013.01); *A61F 2210/0004* (2013.01); *A61F 2210/0076* (2013.01); *A61F 2250/0052* (2013.01); *A61L 2430/02* (2013.01); *A61L 2430/36* (2013.01)

(56) References Cited

U.S. PATENT DOCUMENTS

| | | |
|---|---|---|
| 3,703,897 A | 11/1972 | Mack et al. |
| 3,715,265 A | 2/1973 | Allen et al. |
| 3,849,238 A | 11/1974 | Gould et al. |
| 4,060,081 A | 11/1977 | Yannas et al. |
| 4,077,410 A | 3/1978 | Butterworth et al. |
| 4,187,390 A | 2/1980 | Gore |
| 4,531,916 A | 7/1985 | Scantlebury et al. |
| 4,548,202 A | 10/1985 | Duncan |
| 4,610,250 A | 9/1986 | Green |
| 4,725,234 A | 2/1988 | Ethridge |
| 4,819,478 A | 4/1989 | Melcher |
| 4,849,285 A | 7/1989 | Dillon |
| 4,859,393 A | 8/1989 | Dilllon |
| 4,885,077 A | 12/1989 | Karakelle et al. |
| 4,909,244 A | 3/1990 | Quarfoot et al. |
| 4,923,471 A | 5/1990 | Morgan |
| 4,948,651 A | 8/1990 | Debusk et al. |
| 4,954,388 A | 9/1990 | Mallouk et al. |
| 5,016,622 A | 5/1991 | Norvell |
| 5,017,830 A | 5/1991 | Koike |
| 5,028,332 A | 7/1991 | Ohnishi |
| 5,032,445 A | 7/1991 | Scantlebury et al. |
| 5,036,551 A | 8/1991 | Dailey et al. |
| 5,069,686 A | 12/1991 | Baker et al. |
| 5,082,472 A | 1/1992 | Mallouk et al. |
| 5,093,179 A | 3/1992 | Scantlebury et al. |
| 5,118,524 A | 6/1992 | Thompson et al. |
| 5,171,148 A | 12/1992 | Wasserman et al. |
| 5,196,016 A | 3/1993 | Buser et al. |
| 5,197,882 A | 3/1993 | Jernberg |
| 5,206,028 A | 4/1993 | Li |
| 5,264,214 A | 11/1993 | Rhee et al. |
| 5,334,217 A | 8/1994 | Das |
| 5,356,429 A | 10/1994 | Seare |
| 5,356,432 A | 10/1994 | Rutkow et al. |
| 5,360,341 A | 11/1994 | Abramowitz |
| 5,366,460 A | 11/1994 | Eberbach |
| 5,378,152 A | 1/1995 | Elia |
| 5,405,394 A | 4/1995 | Davidson |
| 5,441,508 A | 8/1995 | Gazielly et al. |
| 5,443,483 A | 8/1995 | Kirsch |
| 5,456,720 A | 10/1995 | Schultz et al. |
| 5,458,636 A | 10/1995 | Brancato |
| 5,480,711 A | 1/1996 | Ruefer |
| 5,496,359 A | 3/1996 | Davidson |
| 5,501,661 A | 3/1996 | Cartmell et al. |
| 5,511,565 A | 4/1996 | Syers |
| 5,545,226 A | 8/1996 | Wingo et al. |
| 5,588,443 A | 12/1996 | Davidson |
| 5,591,234 A | 1/1997 | Kirsch |
| 5,593,441 A | 1/1997 | Lichtenstein et al. |
| 5,607,689 A | 3/1997 | Checchi |
| 5,611,347 A | 3/1997 | Davidson |
| 5,628,790 A | 5/1997 | Davidson et al. |
| 5,632,779 A | 5/1997 | Davidson |
| 5,647,858 A | 7/1997 | Davidson |
| 5,649,951 A | 7/1997 | Davidson |
| 5,658,354 A | 8/1997 | Norvell |
| 5,674,241 A | 10/1997 | Bley et al. |
| 5,700,479 A | 12/1997 | Lundgren |
| 5,716,408 A | 2/1998 | Eldridge et al. |
| 5,728,169 A | 3/1998 | Norvell |
| 5,798,117 A | 8/1998 | New et al. |
| 5,837,278 A | 11/1998 | Geistlich et al. |
| 5,957,690 A | 9/1999 | Bartee et al. |
| 5,968,070 A | 10/1999 | Bley et al. |
| 5,977,428 A | 11/1999 | Bozigian et al. |
| 5,980,540 A | 11/1999 | Bruce |
| 5,993,972 A | 11/1999 | Reich et al. |
| 6,019,764 A | 2/2000 | Bartee |
| 6,022,553 A | 2/2000 | Anders et al. |
| 6,042,534 A | 3/2000 | Gellman et al. |
| 6,060,640 A | 5/2000 | Pauley et al. |
| 6,080,194 A | 6/2000 | Pachence et al. |
| 6,093,201 A | 7/2000 | Cooper et al. |
| 6,113,623 A | 9/2000 | Sgro |
| 6,123,709 A | 9/2000 | Jones |
| 6,143,946 A | 11/2000 | Docter |
| 6,171,329 B1 | 1/2001 | Shaw et al. |
| 6,206,907 B1 | 3/2001 | Marino et al. |
| 6,224,630 B1 | 5/2001 | Bao et al. |
| 6,238,214 B1 | 5/2001 | Robinson |
| 6,244,868 B1 | 6/2001 | Schappert |
| 6,258,124 B1 | 7/2001 | Darois et al. |
| 6,264,702 B1 | 7/2001 | Ory et al. |
| 6,270,530 B1 | 8/2001 | Eldridge et al. |
| 6,277,150 B1 | 8/2001 | Crawley et al. |
| 6,290,708 B1 | 9/2001 | Kugel et al. |
| 6,302,897 B1 | 10/2001 | Rousseau |
| 6,319,264 B1 | 11/2001 | Tormala et al. |
| 6,325,627 B1 | 12/2001 | Ashman |
| 6,328,765 B1 | 12/2001 | Hardwick et al. |
| 6,332,779 B1 | 12/2001 | Boyce et al. |
| 6,383,201 B1 | 5/2002 | Dong |
| 6,394,807 B2 | 5/2002 | Robinson |
| 6,409,764 B1 | 6/2002 | White et al. |
| 6,420,623 B2 | 7/2002 | Augstine et al. |
| 6,441,768 B2 | 8/2002 | Agarwal et al. |
| 6,451,032 B1 | 9/2002 | Ory et al. |
| 6,464,709 B2 | 10/2002 | Shennib et al. |
| 6,497,650 B1 | 12/2002 | Nicolo |
| 6,592,622 B1 | 7/2003 | Ferguson |
| 6,712,859 B2 | 3/2004 | Rousseau et al. |
| 6,736,854 B2 | 5/2004 | Vadurro et al. |
| 7,258,700 B2 | 8/2007 | Lambrecht et al. |
| 7,296,998 B2 | 11/2007 | Bartee et al. |
| 7,547,319 B2 | 6/2009 | Segal et al. |
| 7,651,769 B2 | 1/2010 | Dubrow |
| 7,682,540 B2 | 3/2010 | Boyan et al. |
| 7,789,888 B2 | 9/2010 | Bartee et al. |
| 7,806,911 B2 | 10/2010 | Peckham |
| 7,824,420 B2 | 11/2010 | Eldridge et al. |
| 7,887,593 B2 | 2/2011 | McKay et al. |
| 7,901,461 B2 | 3/2011 | Harmon et al. |
| 7,959,554 B2 | 6/2011 | McAlexander et al. |
| 7,972,360 B2 | 7/2011 | Dean |
| 7,981,022 B2 | 7/2011 | Gellman et al. |
| 8,012,205 B2 | 9/2011 | Plouhar et al. |
| 8,029,286 B2 | 10/2011 | Craig et al. |
| 8,052,753 B2 | 11/2011 | Melvin |
| 2002/0123750 A1 | 9/2002 | Eisermann et al. |
| 2002/0197924 A1 | 12/2002 | Halley et al. |
| 2003/0040809 A1 | 2/2003 | Goldmann et al. |

(56) References Cited

U.S. PATENT DOCUMENTS

| | | |
|---|---|---|
| 2003/0100898 A1 | 5/2003 | Wellisz |
| 2003/0104734 A1 | 6/2003 | Polegato |
| 2003/0105530 A1 | 6/2003 | Pirhonen et al. |
| 2003/0216669 A1 | 11/2003 | Lang et al. |
| 2004/0059418 A1 | 3/2004 | McKay et al. |
| 2004/0215219 A1 | 10/2004 | Eldridge et al. |
| 2004/0224182 A1 | 11/2004 | Lazarev |
| 2004/0232406 A1 | 11/2004 | Weiss et al. |
| 2004/0260340 A1 | 12/2004 | Jacobs et al. |
| 2005/0015088 A1 | 1/2005 | Ringeisen |
| 2005/0023603 A1 | 2/2005 | Eldridge et al. |
| 2005/0079200 A1 | 4/2005 | Rathenow et al. |
| 2005/0083047 A1 | 4/2005 | Lee et al. |
| 2005/0102036 A1 | 5/2005 | Bartee et al. |
| 2005/0164045 A1 | 6/2005 | Rothbrust et al. |
| 2005/0177162 A1 | 8/2005 | McLeod et al. |
| 2006/0200140 A1 | 9/2006 | Lange |
| 2006/0224242 A1 | 10/2006 | Swords et al. |
| 2007/0061015 A1 | 3/2007 | Jensen et al. |
| 2007/0129811 A1 | 6/2007 | Plouhar et al. |
| 2007/0250164 A1 | 10/2007 | Troxel |
| 2007/0260268 A1 | 11/2007 | Bartee et al. |
| 2008/0044449 A1 | 2/2008 | McKay |
| 2009/0076541 A1 | 3/2009 | Chin et al. |
| 2009/0286205 A1 | 11/2009 | Johnson et al. |
| 2010/0217392 A1 | 8/2010 | Bartee et al. |
| 2010/0234880 A1 | 9/2010 | Abbott et al. |
| 2010/0249947 A1 | 9/2010 | Lesh et al. |
| 2010/0312357 A1 | 12/2010 | Levin et al. |
| 2011/0118844 A1 | 5/2011 | Lambrecht |
| 2011/0250565 A1 | 10/2011 | Yarovesky |
| 2011/0264119 A1 | 10/2011 | Bayon et al. |
| 2011/0264120 A1 | 10/2011 | Bayon et al. |
| 2011/0270284 A1 | 11/2011 | Beauchamp et al. |
| 2011/0288567 A1 | 11/2011 | Ranucci et al. |
| 2011/0295283 A1 | 12/2011 | Darois et al. |
| 2013/0035704 A1 | 2/2013 | Dudai |
| 2015/0265407 A1 | 9/2015 | Horvath |
| 2015/0366669 A1 | 12/2015 | Bartee et al. |

OTHER PUBLICATIONS

Gamal et al. "Enhancing guided tissue regneration of periodontal defects by using a novel perforated barrier membrane." J. Periodontol. 84(7):905-913 (Jul. 2013).

Scantlebury, Todd V., "1982-1992: A Decade of Technology Development for Guided Tissue Regeneration", J. Periodontol, vol. 64:1129-1137 (1993).

Vandana et al. "A preliminary study of the guided tissue regeneration procedures for adjacent buccal root coverage using single gtam-tr6t membrane." J. Clin. & Diagnostic Research, vol. 3:1365-1369 (Feb. 2009).

Wilson et al. "Advances in the Use of Guided Tissue Regeneration for Localized Ridge Augumentation in Combination with Dental Implants", Texas Dental Journal vol. 5:7-10 (Jul. 1994).

EP Appln. No. 15173417.5. Applicant: Osteogenics Biomedical Inc. European Search Report, 7 pp. (Oct. 16, 2015).

PCT/US2010/025093. International Search Report (Apr. 22, 2010).

\* cited by examiner

DEVICE FOR GUIDED BONE AND TISSUE REGENERATION

CROSS-REFERENCE TO RELATED APPLICATIONS

The present application for patent is a Continuation of U.S. patent application Ser. No. 15/465,571 entitled "Perforated Membrane For Guided Bone And Tissue Regeneration" filed Mar. 21, 2017, which is a Continuation-in-part of U.S. patent application Ser. No. 14/313,685 entitled "Perforated Membrane For Guided Bone And Tissue Regeneration" filed Jun. 24, 2014, which applications are assigned to the assignee hereof and hereby expressly incorporated by reference herein.

TECHNICAL FIELD

The present disclosure relates to a membrane configured to guide bone and tissue regeneration for a bone defect.

BACKGROUND

It is widely known that the occurrence of tooth loss in human dentition (which may happen as the result of dental diseases, advanced age, genetic inclination, accidents, etc.) is the cause of a number of functional and aesthetic problems. For example, if chewing is unsatisfactory, the entire digestive system may be affected, and the unsatisfactory chewing may cause gastrointestinal dysfunction and complaints. From an aesthetic point of view, properly cared for teeth have considerable significance.

Previously, missing teeth were replaced with a partial denture or a permanently attached dental bridge, supported in part by the remaining natural teeth. Bridges, however, are multi-piece inflexible systems, the shape and color of which do not always conform to expectations, and their participation in the chewing process is also frequently imperfect. Contemporary tooth replacement includes the extraction of damaged or hopeless teeth and implantation titanium implants supported by the patient's own natural bone. If there is inadequate bone for implant support, this bone may be reconstructed using autogenous bone grafts. This, however, is an expensive procedure, which may require hospitalization and in certain cases possible complications. Other options for bone reconstruction include guided tissue regeneration (GTR) and bone regeneration (GBR). Both of these techniques involve the regeneration of bone deficiencies affecting natural teeth by means of barrier membranes. GTR implies the regeneration of the bone and attachment apparatus (ligaments, cementum) of natural teeth, whereas GBR includes the implantation of a membrane into the location where the formation of bone is intended. For either technique, bone and/or bone replacement material is typically used under the membrane. Currently, the membranes used for GTR/GBR do not include macro-perforations in the membrane, but rather are engineered to be cell-occlusive while simultaneously being able to allow the passage of small molecules. It is widely accepted that the membrane functions as a barrier to protect the healing environment form soft tissue ingrowth and resorptive stimuli. The present invention describes modifications to traditional GTR/GBR membranes designed to increase the potential for communication between cells with bone forming potential and the periosteum, while simultaneously providing stability and protection of the three-dimensional envelope of space so that bone may form guided by the final contour of the membrane.

SUMMARY

One aspect of the disclosure relates to a membrane configured to guide bone and tissue regeneration for a bone defect. The membrane may comprise a first layer, a second layer, one or more perforations, a reinforcement binder, and/or other components. The first layer of the membrane may be configured to contact bone. (This is not intended to be limiting. In some situations, a user may place the first layer of the membrane in contact with soft and/or other non-bone tissue). The first layer may include pores configured to promote ingrowth of bone regenerating cells into the first layer. The second layer may be configured to substantially prevent fibrous connective tissue from growing into the bone defect. In some implementations, the second layer may be relatively denser than the first layer. The second layer may comprise a densely woven structure, depending on the material used to make the second layer, for example. The second layer may be fixedly coupled to the first layer. In some implementations, the membrane may be formed from collagen, polytetrafluoroethylene (PTFE), bioresorbable polymer, animal tissue, human tissue, a combination thereof, and/or other materials.

In some implementations, the first layer may consist of a thin layer of expanded PTFE and/or other lightweight mesh polymer materials having a pore size in the range of about 30 microns to about 1000 microns. The first layer may cover the second layer of dense PTFE (for example). This would create a two-layer membrane, one layer being an open-structured mesh and the second being a high density, cell occlusive material.

The one or more perforations may be formed through the membrane. In some implementations, the perforations may be complete through both the first and the second layer. In some implementations, the perforations may comprise co-axial through-holes having common dimensions through the first layer and the second layer. In some implementations (such as when the first layer is a thin layer of expanded PTFE having a pore size in the range of about 30 microns to about 1000 microns as described above), the holes may be complete only though the dense second layer. The perforations may be configured to enhance ossification. In some implementations, the perforations may be substantially circular, and/or have other shapes. In some implementations, the perforations may have a diameter of about 0.1 mm or larger. In some implementations, the perforations may be substantially circular and may have a diameter of about 0.5 mm to about 1.0 mm. In some implementations, a size, a density, a spacing, and/or other characteristics of the perforations may be determined based on one or more of a material that forms the membrane, a thickness of the membrane, a size (e.g., a length and/or a width) of the membrane, and/or other factors.

In some implementations, the membrane may include one or more secondary perforations configured to receive fasteners configured to hold the membrane in place at the bone defect. In some implementations, the fasteners may be pins and/or other fastening devices.

The reinforcement binder may be configured to be placed over the bone defect and coupled with surrounding bone. The reinforcement binder may comprise multiple elongated members extending from a junction. The elongated members may include a first elongated member, for example, having a free end that extends away from the junction with a predrilled hole formed therein. The predrilled hole may be configured to receive a fastener that passes through at least one of the first or second layer of the membrane and holds the membrane in place at the bone defect. In some implementations, the reinforcement binder may be formed between the first layer and the second layer of the membrane. In some implementations, the reinforcement binder may be a titanium reinforcement binder and may be configured to be bent into a desired shape by a user.

Another aspect of the disclosure relates to a method for guiding bone and tissue regeneration for a bone defect with a membrane. The method may comprise forming a first layer of the membrane configured to contact bone and/or other tissue. The first layer may be made from lightweight polymer mesh, collagen, expanded PTFE, and/or other materials. The first layer may be formed with or without perforations (e.g., macropores and/or holes). Whether or not the first layer is formed with perforations, the first layer may include pores configured to promote ingrowth of bone regenerating cells and communication between cells and the periosteum into the first layer. The method may include forming a second layer of the membrane configured to substantially prevent fibrous connective tissue from growing into the bone defect. In some implementations, the second layer may be relatively denser than the first layer. The second layer may comprise a densely woven structure, depending on the material used to make the second layer, for example. The method may comprise fixedly coupling the second layer to the first layer. The method may comprise forming one or more perforations through the membrane. The perforations may comprise co-axial through-holes having common dimensions through the first layer and the second layer. The perforations may be configured to enhance ossification. In some implementations, the perforations may be formed in the second layer only. In some implementations, the membrane may be formed from collagen, polytetrafluoroethylene (PTFE), bioresorbable polymer, animal tissue, human tissue, a combination thereof, and/or other materials.

In some implementations, forming the one or more perforations may include forming the perforations with a substantially circular cross section having a diameter of about 0.1 mm or larger. In some implementations, forming the one or more perforations may include forming the perforations with a substantially circular cross section having a diameter of about 0.5 mm to about 1.0 mm. In some implementations, the method may comprise determining one or more of a size, a density, a spacing, and/or other characteristics of the perforations based on one or more of a material that forms the membrane, a thickness of the membrane, a size of the membrane, and/or other factors.

In some implementations, the method may comprise forming one or more secondary perforations configured to receive fasteners configured to hold the membrane in place at the bone defect. The fasteners may be pins, for example, and/or other fastening devices.

In some implementations, the method may comprise forming a reinforcement binder. The reinforcement binder may comprise multiple elongated members extending from a junction. The elongated members may include a first elongated member, for example, having a free end that extends away from the junction with a predrilled hole formed therein. The method may comprise placing the membrane and the reinforcement binder over the bone defect, receiving a fastener with the predrilled hole that passes through at least one of the first or second layer of the membrane, and coupling the membrane and the reinforcement binder with surrounding bone and holding the membrane in place at the bone defect via the fastener. In some implementations, the reinforcement binder may be formed between the first layer and the second layer of the membrane. In some implementations, the reinforcement binder may be formed from titanium and may receive a shape imparted to the reinforcement binder via bending by a user.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

Figure 1:
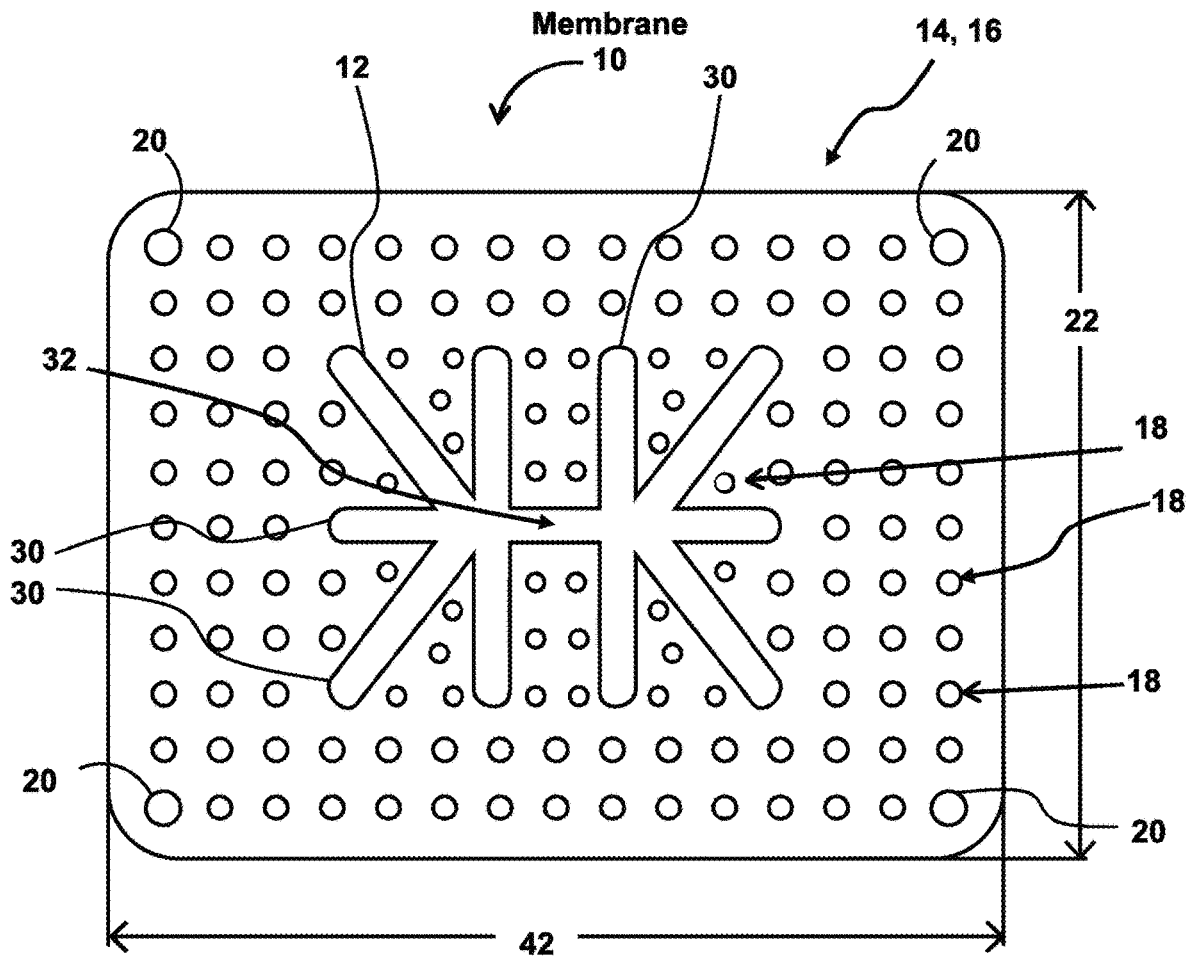
FIG. 1 illustrates a membrane configured to guide bone and tissue regeneration for a bone defect.

FIG. 1 illustrates a membrane 10. Membrane 10 may be configured to guide bone and tissue regeneration for a bone defect. Membrane 10 may be suitable for guided bone regeneration (GBR), guided tissue regeneration (GTR), and/or other therapies. Membrane 10 may form a barrier membrane used for guiding bone and tissue regeneration for dental and/or other purposes. Membrane 10 may be used in oral surgery, maxillofacial surgery, craniofacial surgery, to treat periodontal diseases, for dental implants, to treat orbital floor bone defects, and/or for other applications. Membrane 10 may be configured to maintain space for bone regeneration, to prevent connective tissue fibers from growing into the bone tissue, to immobilize bone, to exclude stimuli, which may hinder bone generation, and/or for other purposes. Membrane 10 may be a barrier membrane that is applicable in alveolar ridge defect replacements and/or for other defects that membrane 10 is sized to cover. Membrane 10 may facilitate reducing and/or eliminating injuries, and/or facilitate a more efficient bone and tissue regeneration process compared to previously known techniques. Membrane 10 may include perforations 18 located at various distances from each other throughout membrane 10.

Perforations 18 in membrane 10 may be based on the surprising discovery that if a barrier membrane does not constitute a continuous surface at the location of the desired bone and tissue regeneration (e.g. if the membrane includes perforations that are larger than a pore size in a surface of the membrane) the membrane still induces a positive effect on bone regeneration, especially when combined with the use of various biological growth factors. Membranes with perforations have been shown to better facilitate bone regeneration than membranes without perforations. The perforated design also makes the membrane easier to handle, fixate, and/or shape during application because the surgeon may more readily visualize, for example, pilot holes made specifically for the purpose of securing membrane fixation screws, pins or tacks.

A perforated membrane may facilitate communication between a patient's periosteum and growth factors used with GBR. The growth factors may include RhPDGF (Platelet Derived Growth Factor), RhBMP (Bone Morphogenetic Protein), and/or other growth factors. The perforations may also facilitate communication between the periosteum and undifferentiated stem cells, especially in the presence of simulative growth factors. Application of a non-perforated collagen (for example) membrane may reduce the regenerative potential of PDGF. If a surgeon (and/or other users) utilizes ground autogenous bone for bone generation, which makes the application of a membrane necessary, the "permeability" of a perforated membrane may make the development of a connection with the periosteal membrane possible using the PDGF technique.

Similarly, membrane 10 may be used with RhBMP. Using membrane 10 with RhBMP may allow a surgeon (and/or other users) to avoid using a titanium net/mesh (used for its permeability relative to a non-perforated membrane), for example. A titanium net/mesh may cause complications because it is sharp and difficult to handle. Such complications may include, for example, damaging the gum of a patient or difficult removal (taking as long as thirty minutes). Conversely, membrane 10 may be removable in a matter of a few minutes, which decreases the duration of surgery and the possible occurrences of complications.

Continuing with the above non-limiting example comparison to the titanium net/mesh, the present invention differs from titanium mesh in several respects. These include mechanical compliance, placement, removal, customization, and/or other differences. (1) Mechanical Compliance: perforated PTFE is more flexible, and therefore has improved compliance with soft tissue compared to titanium mesh. Mechanical compliance is important because biomaterials that are compliant with soft tissue have a much less reduced risk of soft tissue dehiscence (opening) and/or wound healing complications. (2) Placement: because of its flexibility and softness, membrane 10 easier to adapt, place, and/or fixate compared to titanium mesh. (3) Removal: regenerated bone tends to grow through and/or over the titanium mesh struts, making it exceedingly difficult to remove. During removal of titanium mesh, damage to the immature regenerated bone may occur, resulting in less volume of regenerated tissue than desired. In contrast, with membrane 10 being flexible, it is much easier to remove and in fact is able to stretch and therefore presents less risk of damaging the newly formed bone tissue as the device is removed. (4) Customization: relating to method, in a 'custom fit' application, the present invention is much easier to trim and cut, and/or the surgeon may easily punch holes directly at the time of surgery with a simple hand punch, enabling the creation of a truly custom surgical device for individual defects. The surgeon may place the holes in exactly the location desired, and they may make more holes, or fewer holes depending on the clinical indication. For example, it may be advantageous in a case where membrane exposure was desired, to leave the exposed portion non-perforated and to create perforations in the areas where communication between the periosteum and graft bed was desired. This maneuver would be exceedingly difficult to accomplish with a sheet of titanium.

Figure 2:
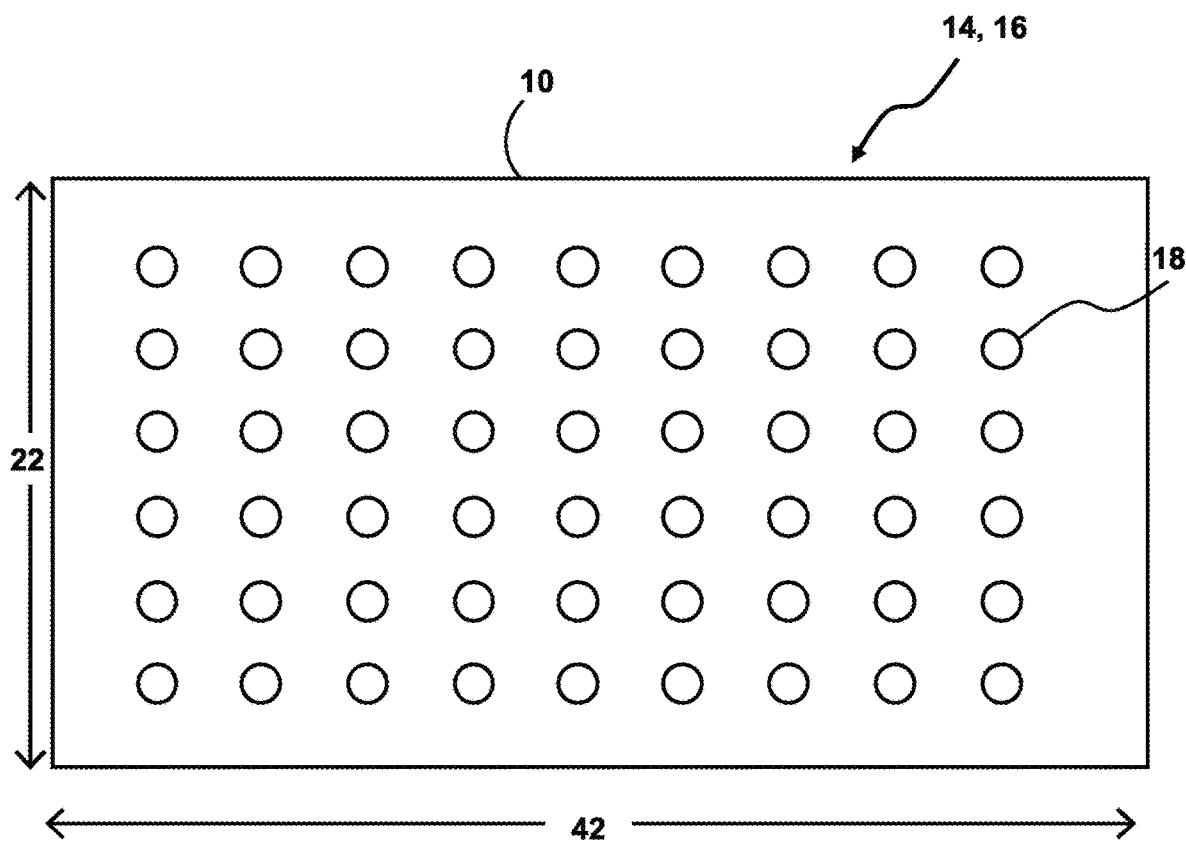
FIG. 2 illustrates a membrane without a reinforcement binder.

In some implementations, membrane 10 may include a first layer 14 (FIG. 3), a second layer 16 (FIG. 4), one or more perforations 18, a reinforcement binder 12, and/or other components. In some implementations, the first layer may be non-perforated, and consist of a thin layer of lightweight polymer mesh, collagen or expanded PTFE. In some implementations, the perforations may only be complete through a single layer of the membrane, with the layer of lightweight polymer mesh, collagen, or expanded PTFE bonded (for example) to it. Said membrane may or may not contain a titanium framework between the layers. In some implementations, membrane 10 may not include reinforcement binder 12. For example, FIG. 2 illustrates membrane 10 without reinforcement binder 12. First layer 14, second layer 16, reinforcement binder 12, and/or other components of membrane 10 may be similar to and/or the same as similar components described in U.S. Pat. No. 8,556,990 granted on Oct. 15, 2013, and entitled, "Reinforced PTFE Medical Barriers," which is hereby incorporated herein by reference in its entirety.

As shown in FIG. 2, membrane 10 may be generally rectangular and have a length 42 and a width 22. In some implementations, length 42 may be less than about 50 mm. Length 42 may be between about 30 mm and about 50 mm. Length 42 may be about 40 mm. In some implementations, width 22 may be less than about 40 mm. Width 22 may be between about 20 mm and about 40 mm. Width may be about 30 mm. In some implementations, membrane 10 may have a thickness from about 0.125 mm to about 0.25 mm. The generally rectangular shape and approximate dimensions of membrane 10 shown in FIG. 2 are not intended to be limiting. Membrane 10 may take any shape and have any dimensions that allow it to function as described in the present disclosure.

In some implementations, membrane 10 may be formed from collagen, polytetrafluoroethylene (PTFE), and/or other materials, and/or a combination of materials. In some implementations, membrane 10 made be formed from one or more of expanded PTFE, unsintered PTFE, high density PTFE, and/or other materials. In some implementations, one or more layers 14, 16 (FIG. 3 and FIG. 4) of membrane 10 (e.g., second layer 16) may be formed from unsintered substantially unexpanded PTFE. The term sintered is a term well known in the art and is used herein consistent with that understanding. The term unsintered is used herein to describe PTFE polymer that has not been subjected to the sintering process. Unsintered PTFE may be substantially unexpanded and typically contains no substantially defined internodal distance, which may substantially reduce its porosity relative to expanded PTFE. The limited porosity of the unsintered, substantially unexpanded PTFE may substantially reduce tissue adhesion to the unexpanded PTFE and/or migration of tissue into the unexpanded PTFE. However, the limited porosity may allow for the passage of ions and other small molecules necessary for cellular nourishment and waste transport. In some implementations, a density of one or more layers 14, 16 (FIG. 3 and FIG. 4) of membrane 10 may be about 1.2 gm/cc to about 2.3 gm/cc. In some implementations, the density of one or more layers 14, 16 of membrane 10 may be about 1.45 gm/cc to about 1.55 gm/cc.

Figure 3:
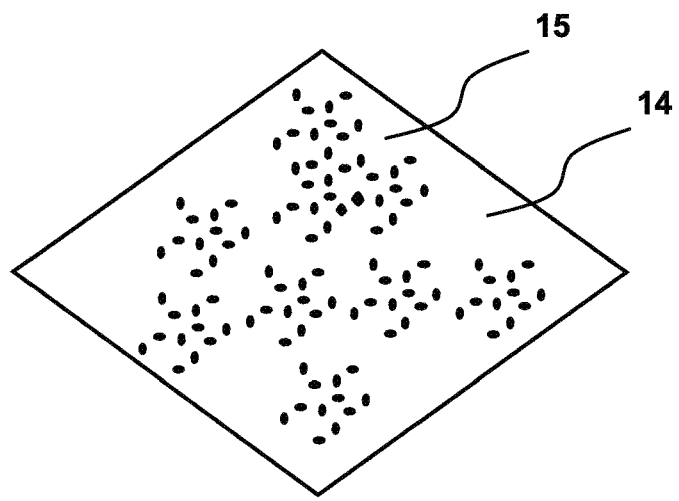
FIG. 3 illustrates first layer of the membrane.
Figure 4:
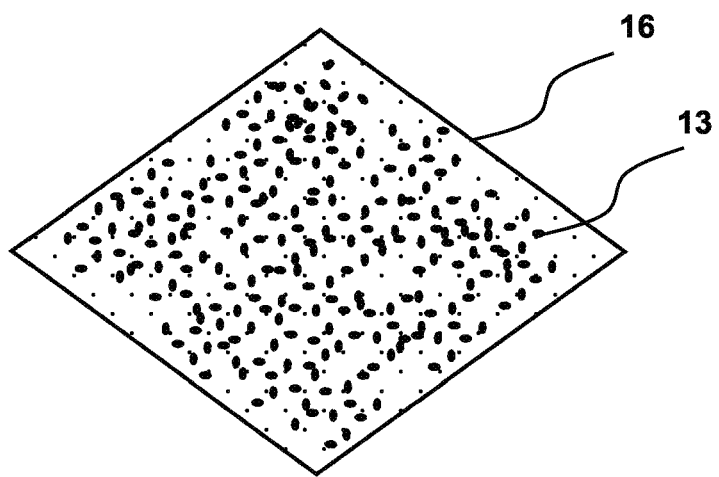
FIG. 4 illustrates a second layer of the membrane.

FIG. 3 illustrates first layer 14 and FIG. 4 illustrates second layer 16. First layer 14 may be configured to contact bone. (This is not intended to be limiting. In some situations, a user may place the first layer of the membrane in contact with soft and/or other non-bone tissue. For example, surgeons may choose to place the expanded PTFE layer or the dense PTFE layer towards bone, or soft tissue). First layer 14 may include pores 15 configured to promote ingrowth of bone regenerating cells into first layer 14. Second layer 16 may be fixedly coupled to first layer 14 and/or be coupled to first layer 14 in other ways. Second layer 16 may be configured to substantially prevent fibrous connective tissue from growing into the bone defect. Second layer 16 may comprise a dense structure that prevents tissue ingrowth. Second layer 16 may be relatively denser than first layer 14, for example. First layer 14 and second layer 16 may be separate layers of membrane 10 (as described above), and/or first layer 14 and second layer 16 may be two surfaces on opposite sides of membrane 10 (e.g., opposite sides of a single layer).

The pores in materials used to construct the first layer 14 and/or the second layer 16 may be formed during manufacture of the materials. Pores may be formed due to the presence of expanded gases, material deformations and other cause during manufacture. For example, pores may be formed as a cavity in a material forming a layer 14, 16 of the membrane 10. The pores may be caused during manufacture when gases in the material expand to form a bubble. In one example, pores may be formed in expanded polytetrafluoroethylene (ePTFE), and the pores may range in size from 30 microns to 500 microns. Processes employed in the manufacture of an ePTFE material may be adapted to cause formation of pores of a desired size and distribution throughout at least a portion of the ePTFE material. The pores in the ePTFE material may be configured to promote ingrowth of bone regenerating cells into the first layer. Other layers 14, 16 may comprise a high density, cell occlusive PTFE configured to substantially prevent fibrous connective tissue from growing into the bone defect. In some instances, the cell occlusive PTFE has a dense structure. The cell occlusive PTFE may be fixedly coupled to the ePTFE layer.

By way of a non-limiting example, first layer 14 may be and/or include expanded PTFE (e-PTFE). Second layer 16 may be and/or include unsintered high density PTFE (d-PTFE) having a density of about 1.2 gm/cc to about 2.3 gm/cc. In some implementations, the density of d-PTFE may be in a range from about 1.45 grams/cc to about 1.55 grams/cc. The d-PTFE material may be unsintered and unexpanded with a nominal pore channel 13 size of less than about 5 micrometers. In some implementations, the unsintered, unexpanded d-PTFE may have a nominal pore channel 13 size of less than about 2 micrometers. In some implementations, the unsintered, unexpanded d-PTFE may have a nominal pore channel 13 size of less than about 0.5 micrometers. In some implementations, the unsintered, unexpanded d-PTFE may have a nominal pore channel 13 size of less than about 0.2 micrometers. This small pore channel size may allow a composite multi-layer material employing d-PTFE to exhibit superior functional characteristics, resulting clinically in reduced host response (inflammation), soft tissue in-growth, and resultant adhesions. (These pore channel 13 sizes may be smaller than pore 15 sizes in first layer 14 made from e-PTFE that promote bone ingrowth.)

Figure 5:
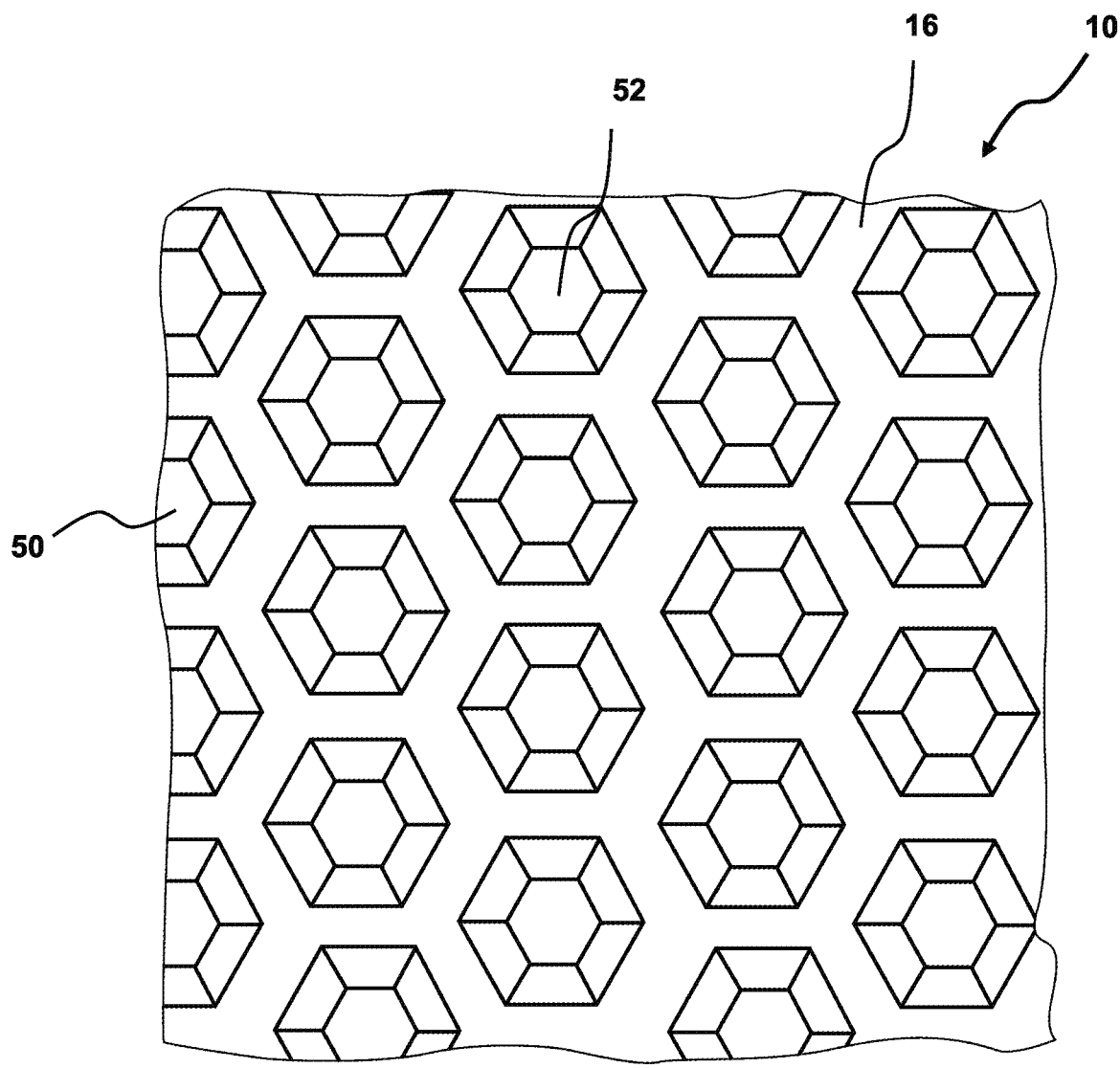
FIG. 5 illustrates a texture pattern formed in the second layer of the membrane.

FIG. 5 illustrates a texture pattern 50 that may be formed in second layer 16 of membrane 10. The texture pattern may be formed by a plurality of indentations 52 formed in second layer 16 of membrane 10. Indentations 52 may have any shape that allows membrane 10 to function as described herein. The example shown in FIG. 5 is hexagonal in shape, although other shapes are contemplated and fall within the scope of this disclosure. The indentations may have a depth less than the thickness of second layer 16. In some implementations, indentations 52 may be up to about 0.15 mm deep and up to about 0.5 mm wide, for example. Indentations 52 may be dimensioned based on the intended use for membrane 10 and/or other factors. The distribution of indentations 52 may be substantially uniform over second layer 16, may vary systematically across second layer 16, may be randomly distributed across second layer 16, and/or have other distributions. For example, up to about 150 indentations may be provided per square centimeter over second layer 16. As another example, up to about 250 indentations may be provided per square centimeter over second layer 16.

Texture pattern 50 of second layer 16 may be made by forming a thin sheet of PTFE and then embossing the sheet with indentations. PTFE resin may be mixed with a lubricant (e.g., mineral spirits) to form a paste. The paste may be calendered between rollers to form a thin flat sheet of the desired thickness (e.g., in the range of about 0.125 mm to about 0.25 mm.) The calendering may be performed to reduce the thickness of the sheet and to impart substantially uniform strength in all directions to the sheet. The lubricant may be removed by drying the sheet at a temperature somewhat above the boiling point of the mineral spirit lubricant, but well below the sintering temperature of PTFE. After the sheet has been dried, the sheet may be embossed to form the indentations in one of its surfaces. In some implementations, the embossing step may be performed by placing a sheet of patterned polymer mesh on top of the sheet of PTFE. The patterned polymer mesh may be harder and have more compressive strength than the PTFE material. In some implementations, the polymer mesh may be a suitable commercially available fine pore-size mesh material. The polymer mesh and the PTFE sheet may be passed together between a pair of rollers, which emboss the pattern of the polymer mesh into one surface of the PTFE sheet. After embossing, the polymer sheet may be discarded. One of many possible advantages of the textured surface is to increase the surface area available for cell attachment.

Returning to FIG. 1, perforations 18 may comprise coaxial through-holes having common dimensions through first layer 14 and second layer 16. (In some implementations, as described herein, perforations may only be located in the second layer, with the first layer being continuous, and fabricated of lightweight polymer mesh, collagen or expanded PTFE, for example.) Perforations 18 may be configured to enhance ossification. In some implementations, perforations 18 may have a substantially circular shape. In some implementations, perforations 18 may have a substantially circular cross section. In some implementations, perforations 18 may have a form factor other than circular. For example, perforations may be substantially shaped as a square, a rectangle, a triangle, a diamond, an oval, a pentagon, a hexagon, an octagon, a free form shape, and/or other shapes. In some implementations, one or more perforations 18 may be and/or include perforations with a substantially circular cross section having a diameter of about 0.1 mm or larger. In some implementations, one or more perforations 18 may be and/or include perforations with a substantially circular cross section having a diameter of about 0.5 mm to about 1.0 mm. In some implementations, one or more perforations 18 may be and/or include perforations with a substantially circular cross section having a diameter of up to about 3.0 mm. In some implementations, the shape and/or size of perforations 18 may vary across membrane 10. For example, perforations 18 may be smaller near reinforcement binder 12 and larger near the edges of membrane 10.

The shapes and/or dimensions of the perforations described above are not intended to be limiting. Perforations 18 may have any size and/or shape that allows them to function as described herein. In some implementations, a size, a shape, a density, a spacing, and/or other characteristics of perforations 18 may be determined based on one or more of a material that forms membrane 10, a thickness of membrane 10, a size (e.g., length and width) of membrane 10, a shape and/or size of reinforcement binder 12, an intended use for the membrane, and/or other factors.

In some implementations, membrane 10 may be configured such that perforations 18 may be formed at manufacture, formed by a user (e.g., a surgeon, a doctor, a nurse, and/or other clinicians), and/or formed at other times. In some implementations, perforations 18 may be formed during an individual procedure according to the needs of the patient and/or the bone defect. For example, a user may use a sharp tool to pierce or perforate membrane 10, a tool associated with membrane 10, and or other devices to make perforations 18. In such implementations, the number and/or the spacing of the perforations may be determined by the user. In such implementations, the shape of perforations 18 may depend on the tool used to make the perforations.

In some implementations, one or more secondary perforations 20 may be formed in membrane 10. Secondary perforations 20 may be configured to receive fasteners configured to hold membrane 10 in place at the bone defect. Secondary perforations 20 may have a different size, shape, and/or density relative to perforations 18. The fasteners may be pins (e.g., Titanium Master Pins manufactured by the Meisinger corporation), titanium tacks, screws (e.g., manufactured by Pro-Fix, Osteogenics, etc.), and/or other fastening devices.

Reinforcement binder 12 may comprise multiple elongated members 30 extending from a junction 32. In some implementations reinforcement binder 12 may be formed between first layer 14 and second layer 16 of membrane 10. In some implementations, reinforcement binder 12 may be formed from titanium, stainless steel, platinum, ceramics, composites, carbon fiber materials, customized micro and/or nano material based materials, coated (e.g., with a non-toxic coating) materials, and/or other materials. Reinforcement binder 12 may be bendable and may include elongate members 30 such that reinforcement binder 12 may be formed in a desired shape (e.g. at manufacture), and/or may be bent, deformed, and/or reformed by a user to obtain the desired shape prior to placement about the bone defect such that the formed shape is maintained upon placement. For example, one or more portions and/or all of reinforcement binder 12 may be bent, twisted, and/or stretched as necessary to obtain the desired shape. In some implementations, reinforcement binder 12 may be malleable and/or flexible because it is relatively thin. For example, a thin piece of titanium may be easily bent by a user.

Figure 6:
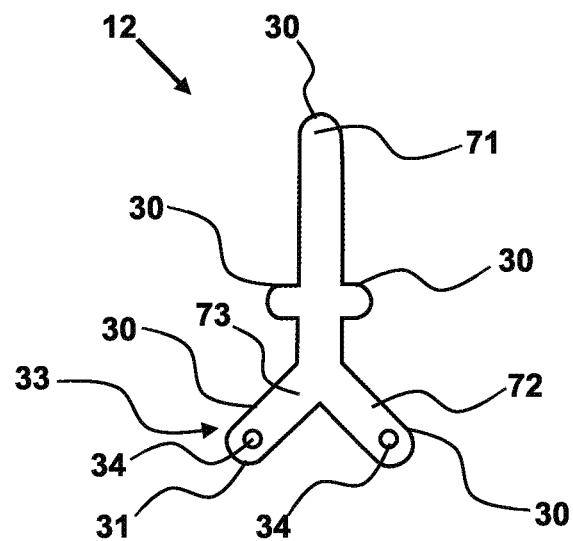
FIG. 6 illustrates an example implementation of a reinforcement binder.
Figure 7:
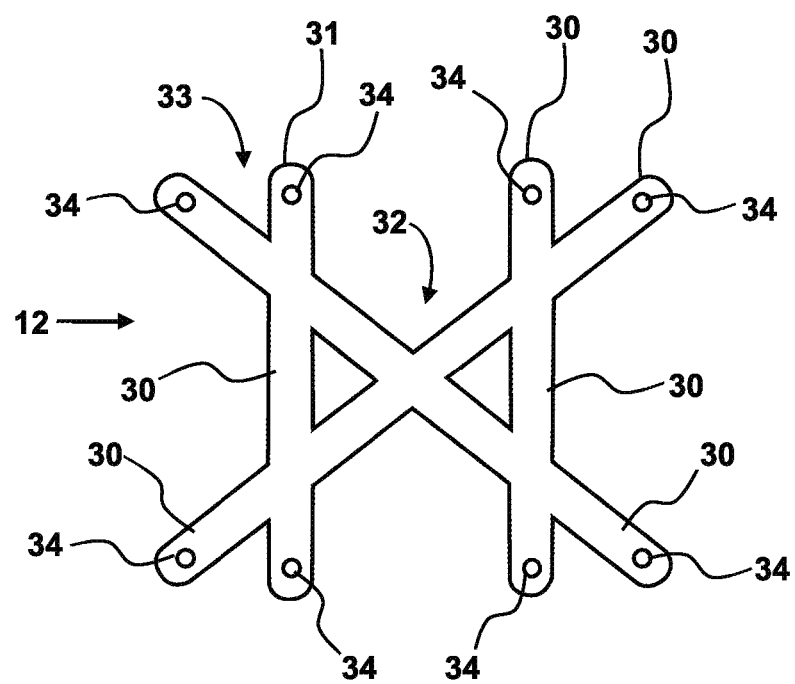
FIG. 7 illustrates an example implementation of the reinforcement binder.

As shown in FIG. 6 and FIG. 7, elongated members 30 may include a first elongated member 31, for example, having a free end 33 that extends away from junction 32 with a predrilled hole 34 formed therein. In some implementations, one or more elongated members 30 may include predrilled holes 34. The pre-drilled holes may be suitable for securing a fastener such as a surgical pin or screw to the bone defect site. Reinforcement binder 12 may be placed over a bone cavity, such as an alveolar cavity, for example. FIG. 6 illustrates an example of reinforcement binder 12 which has an elongate member 71, for placement over a cavity toward a lingual side of the cavity. FIG. 6 illustrates two elongate members 72 and 73 in a "Y-shaped configuration" at an opposite end of reinforcement binder 12, both having holes 34 for securing a fastener. The fastener may be a surgical screw, for example, configured to fasten membrane 10 to an area of bone, typically at a surgical site, for example on the buccal side of the jaw, or upper alveolar arch, in the repair of alveolar defects and/or maxillofacial defects, for example.

Layers 14 and 16 (FIGS. 3 and 4) may be coupled with reinforcement binder 12. Coupling may include fixing, attaching, and/or otherwise joining the layers and reinforcement binder 12 together. Layers 14, 16 and reinforcement binder 12 may be coupled using any suitable means, including use of an adhesive layer for attachment and/or bonding the layers 14, 16 and reinforcement binder 12. Layers 14, 16 may partially cover reinforcement binder 12. Layers 14, 16 may substantially envelope reinforcement binder 12.

Dimensions of reinforcement binder 12 may be selected based on the application (e.g., based on the bone defect to be treated). Similarly, the physical and mechanical properties of reinforcement binder 12 may be selected according to application. Titanium is used as the primary example herein. Surgical grade titanium may be used to provide malleability, strength, and low weight. It should be appreciated that titanium possesses strength and weight characteristics that, together with the biologically inert nature of the metal, offers advantages in many applications. It is contemplated that some applications may dictate that other dimensions, ratios of dimensions, and/or materials may be employed. For example, repair of bone material in a pelvis and/or a hip may require the use of steel and/or other materials.

The structural configuration of reinforcement binder 12 may be selected to facilitate ease of placement and/or use in reconstructive repair of bone defects of various sizes, related soft tissue repair, and/or skeletal surgery, for example. The structural configuration of reinforcement binder 12 may be selected to provide one or more appendages and/or elongate members suitable for placement about bone and/or surrounding tissue. The overall shape of reinforcement binder 12 may be selected to achieve a desired strength, load distribution, membrane support, placement of fasteners, comfort, ease of insertion and/or removal, and/or achieve other effects.

Membrane 10 and reinforcement binder 12 may be implemented at the bone defect. Implementing membrane 10 and reinforcement binder 12 at the bone defect may comprise placing membrane 10 and reinforcement binder 12 over the bone defect, receiving a fastener with the predrilled hole that passes through at least one of first layer 14 or second layer 16 of membrane 10, coupling membrane 10 and reinforcement binder 12 with surrounding bone, holding membrane 10 in place at the bone defect via the fastener, and/or other operations. In some implementations, reinforcement binder 12 may receive a shape imparted to reinforcement binder 12 via bending by a user (e.g., a surgeon). Membrane 10 may be placed over and/or about a bone defect (e.g., a bone cavity) and/or a target surgical site with the unsintered, textured d-PTFE (second layer 16) facing soft tissue (e.g., gingival tissue) and the expanded e-PTFE (first layer 14) facing and/or adjacent to the bone and/or skeletal cavity. This is not intended to be limiting. In some implementations, if a surgeon (for example) desires, and/or if the clinical situation dictates, the aforementioned orientation may be reversed such that second layer 16 faces bone and first layer 14 faces soft tissue.

Figure 8:
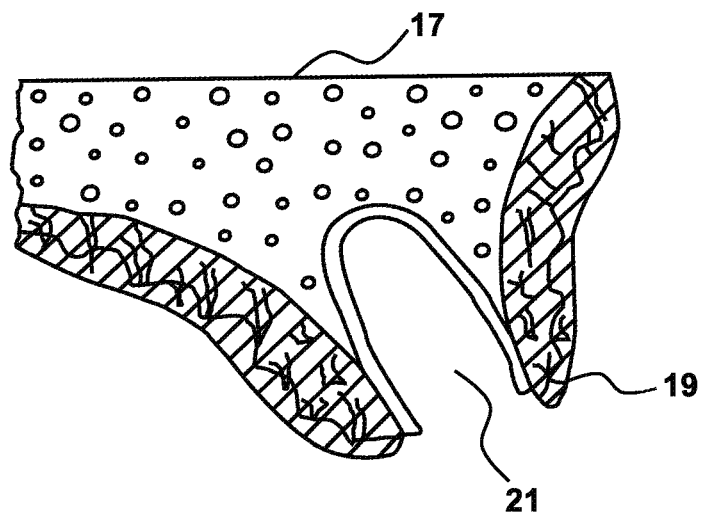
FIG. 8 is a lateral cross-sectional view of an adult human maxilla after a tooth extraction showing alveolar bone.
Figure 9:
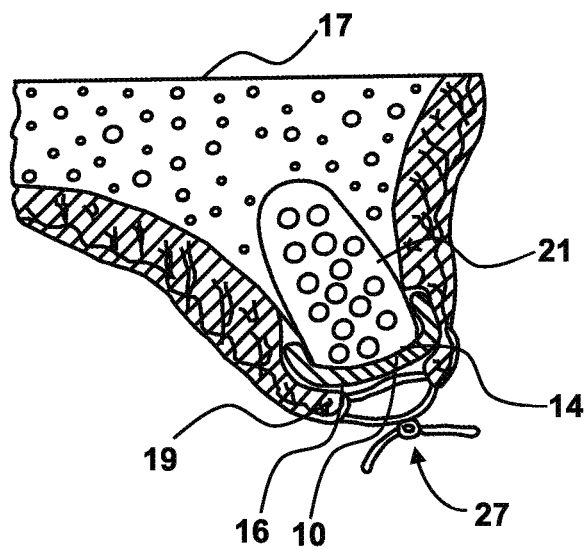
FIG. 9 shows a tooth socket packed with bone and covered with a membrane.
Figure 10:
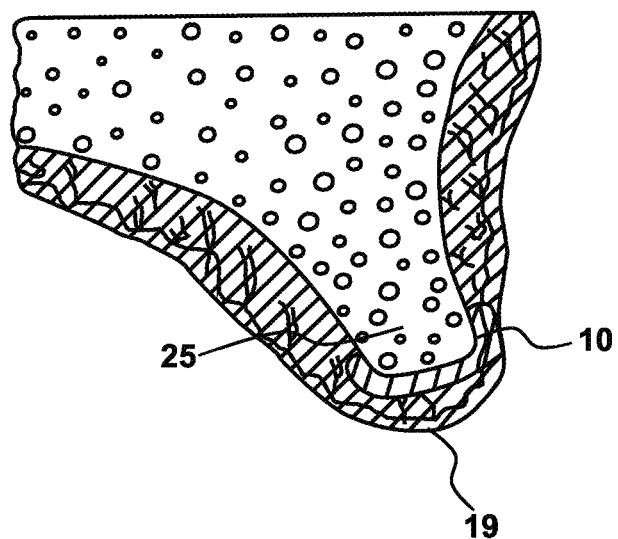
FIG. 10 shows a typical tooth extraction site after healing, but prior to removal of a membrane.

For example, FIGS. 8-10 show examples of implementing membrane 10 at a bone defect. FIG. 8 is a lateral cross-sectional view of an adult human maxilla after a tooth extraction showing alveolar bone 17. Soft tissue gingiva 19 covers bone 17. A tooth socket 21 provides an example of a bone defect. Normal healing of a defect may include migration of cells such as fibroblasts and gingival epithelial cells, for example. As the cells proliferate into defect 21, they may inhibit bone cell regeneration, which may result in overall loss of bone mass. In the case of extractions, the loss of bone mass may result in a loss of the alveolar ridge profile.

FIG. 9 shows socket 21 packed with bone and covered with membrane 10. Socket 21 may be packed with granular particles of allograft, xenograft and/or bioresorbable hydroxyapatite, for example, as a precursor to bone, and/or other materials. Other materials and/or articles, such as endosseous type dental implants, may be placed into socket 21. The packed socket 21 may be covered with membrane 10. First layer 14 may be placed over and/or facing socket 21 and/or bone 17. Second layer 16 may face and/or contact tissue 19 growing over and/or around membrane 10. After membrane 10 is placed over socket 21 and bone 17, membrane 10 (e.g., reinforcement binder 12) may be secured in place via fasteners (not shown). Gingival flaps 19 may be sutured 27 over membrane 10. Membrane 10 may hold the hydroxyapatite particles and/or other materials in place in socket 21 during healing and prevent migration of cells and/or connective tissue into socket 21. However, connective tissue (e.g., gingival tissue 19) may form a weak attachment with the textured surface of second layer 16, without growing through membrane 10. The attachment may be weak enough that membrane 10 may be removed after healing without significant trauma but may be strong enough to prevent dehiscence.

FIG. 10 shows a typical tooth extraction site after healing, but prior to removal of membrane 10. As shown in FIG. 10, the alveolar ridge profile 25 may be preserved and the gingival tissue 19 may be completely healed over ridge 25. Membrane 10 may be removed by making a small incision (not shown) in gingival tissue 19 to expose a portion of layer 23. The layer 23 may then be pulled out with forceps or the like. The material may typically be easily pulled out without trauma to the patient because the attachment of the connective tissue to the textured surface is weak.

Figure 11:
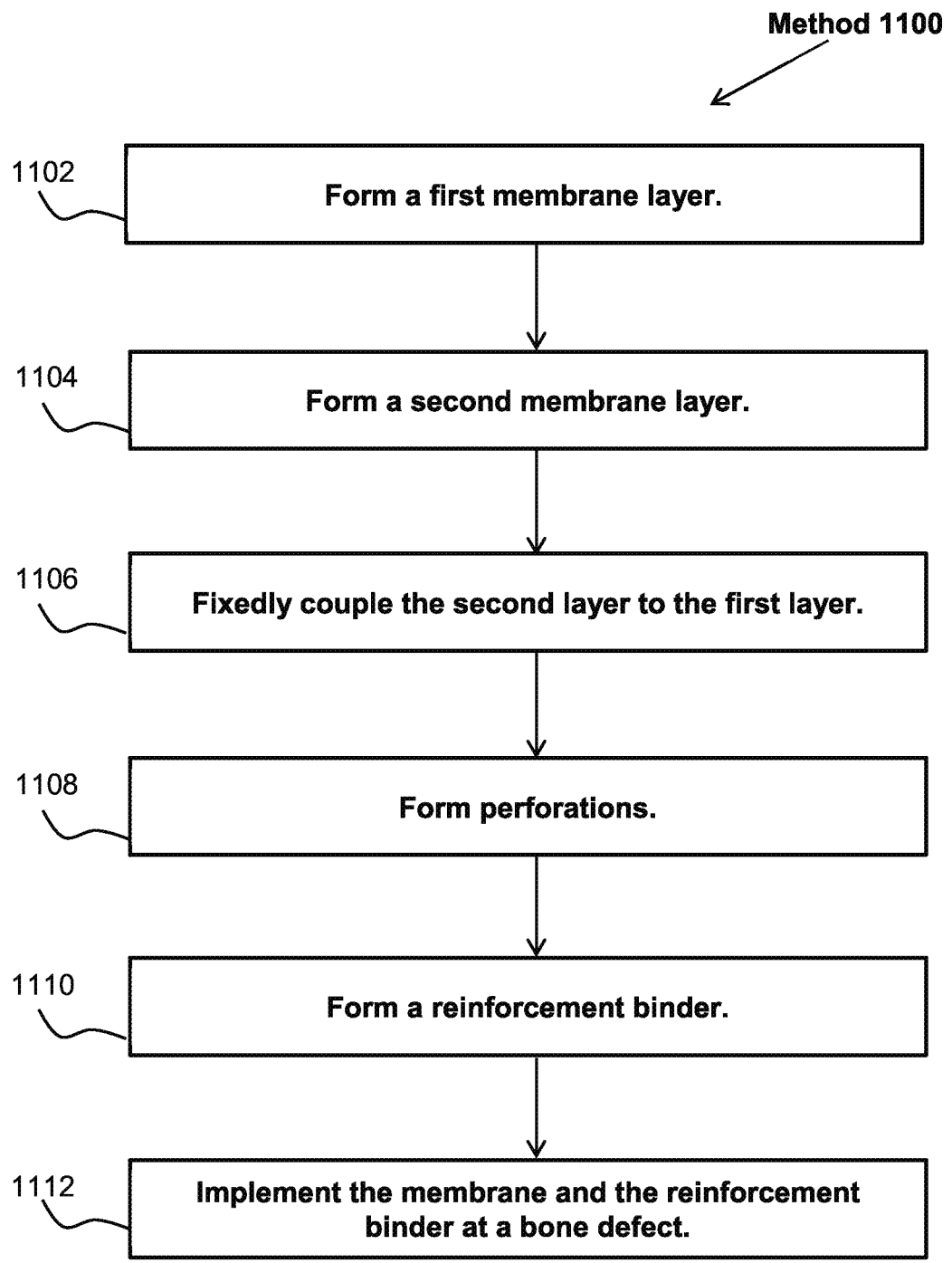
FIG. 11 illustrates a method for guiding bone and tissue regeneration for a bone defect with a membrane.

FIG. 11 illustrates a method 1100 for guiding bone and tissue regeneration for a bone defect with a membrane. In some implementations, the membrane may be formed from collagen, polytetrafluoroethylene, and/or other materials. The operations of method 1100 presented below are intended to be illustrative. In some implementations, method 1100 may be accomplished with one or more additional operations not described, and/or without one or more of the operations discussed. Additionally, the order in which the operations of method 1100 are illustrated in FIG. 11 and described herein is not intended to be limiting.

At an operation 1102, a first layer of the membrane configured to contact bone may be formed. The first layer may include pores configured to promote ingrowth of bone regenerating cells into the first layer. In some implementations, operation 1102 may be performed by a layer the same as or similar to first layer 14 (shown in FIG. 3 and described herein).

At an operation 1104, a second layer of the membrane configured to substantially prevent fibrous connective tissue from growing into the bone defect may be formed. In some implementations, the second layer may be relatively denser than the first layer. The second layer may comprise a densely woven structure, depending on the material used to make the second layer, for example. In some implementations, operation 1104 may be performed by a layer the same as or similar to second layer 16 (shown in FIG. 4 and described herein).

At an operation 1106 the second layer may be fixedly coupled to the first layer. In some implementations, operation 1106 may be performed by layers the same as or similar to second layer 16 (shown in FIG. 4 and described herein) and first layer 14 (shown in FIG. 3 and described herein).

At an operation 1108, one or more perforations through the membrane may be formed. The perforations may comprise co-axial through-holes having common dimensions through the first layer and the second layer. The perforations may be configured to enhance ossification. In some implementations, forming the one or more perforations may include forming the perforations with a substantially circular cross section having a diameter of about 0.1 mm or larger. In some implementations, forming the one or more perforations may include forming the perforations with a substantially circular cross section having a diameter of about 0.5 mm to about 1.0 mm. In some implementations, operation 1108 may comprise determining one or more of a size, a density, a spacing, and/or other characteristics of the perforations based on one or more of a material that forms the membrane, a thickness of the membrane, a size of the membrane, and/or other factors. In some implementations, operation 1108 may comprise forming one or more secondary perforations configured to receive fasteners configured to hold the membrane in place at the bone defect. The fasteners may be pins, for example, and/or other fastening devices. In some implementations, operation 1108 may be performed by perforations the same as or similar to perforations 18 (shown in FIG. 1 and described herein).

At an operation 1110, a reinforcement binder may be formed. The reinforcement binder may comprise multiple elongated members extending from a junction. The elongated members may include a first elongated member, for example, having a free end that extends away from the junction with a predrilled hole formed therein. In some implementations, operation 1110 may be performed by a reinforcement binder the same as or similar to reinforcement binder 12 (shown in FIG. 1 and described herein).

At an operation 1112, the membrane and the reinforcement binder may be implemented at the bone defect. Implementing the membrane and the reinforcement binder at the bone defect may comprise placing the membrane and the reinforcement binder over the bone defect, receiving a fastener with the predrilled hole that passes through at least one of the first or second layer of the membrane, and coupling the membrane and the reinforcement binder with surrounding bone and holding the membrane in place at the bone defect via the fastener. In some implementations, the reinforcement binder may be formed between the first layer and the second layer of the membrane. In some implementations, the reinforcement binder may be formed from titanium and may receive a shape imparted to the reinforcement binder via bending by a user. In some implementations, operation 1112 may be performed by a membrane the same as or similar to membrane 10 (shown in FIG. 1 and described herein) and a reinforcement binder the same as or similar to reinforcement binder 12 (shown in FIG. 1 and described herein).

Figure 12:
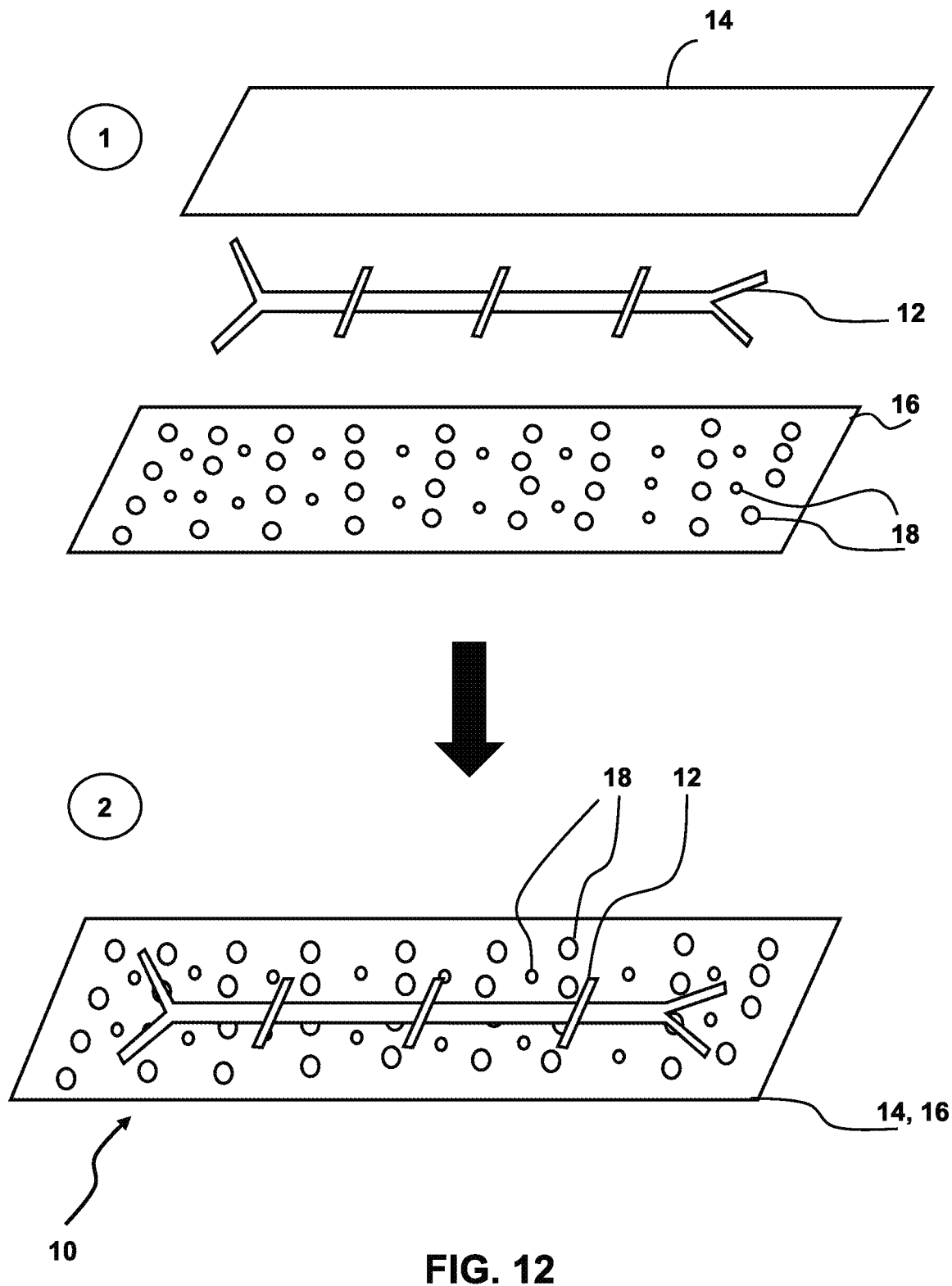
FIG. 12 illustrates an example of the membrane wherein the second layer includes perforations but the first layer does not.

As described above and illustrated in FIG. 12, in some implementations, membrane 10 may be configured such that first layer 14 is a thin layer of expanded PTFE (and/or other lightweight mesh polymer material and/or collagen) having pores in a size range of about 30 microns to about 1000 microns, but no perforations. In these implementations, first layer 14 is not perforated, but rather covers second layer 16 of dense PTFE, which is perforated (e.g., perforations 18). These implementations may create a (e.g., laminated) two-layer membrane, with one layer (e.g., first layer 14) comprising an open-structured mesh and the second layer (e.g., second layer 16) comprising a high density, cell occlusive material. Such implementations may still allow communication of large molecules between the periosteum and the underlying bone graft, just as when perforations 18 are through both layers of membrane 10. As shown in FIG. 12, such implementations, may include a reinforcement binder 12 (e.g., a flexible titanium reinforcement binder) as described herein.

Figure 13:
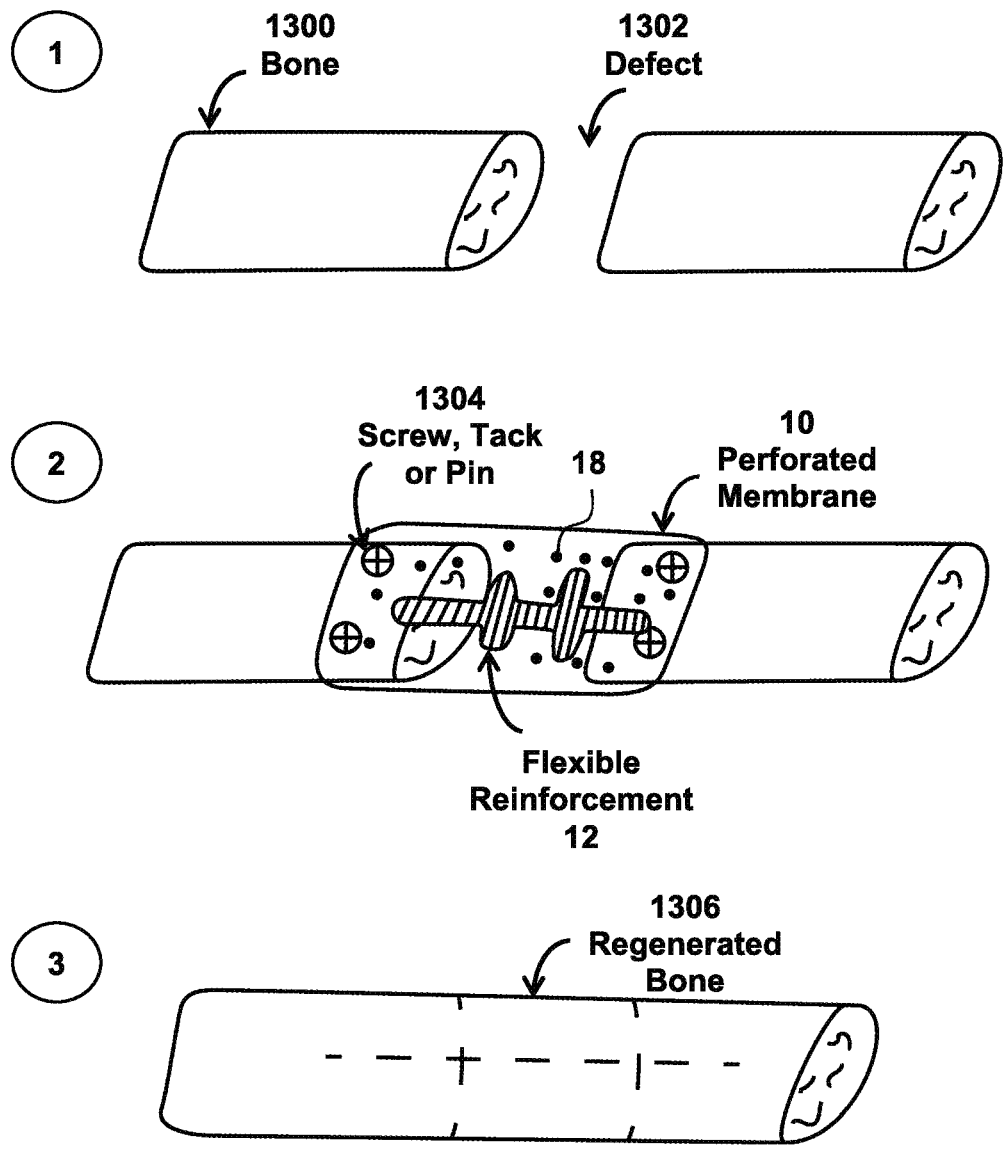
FIG. 13 illustrates treatment of a discontinuity defect with the membrane.

FIG. 13 illustrates treatment of a discontinuity defect with membrane 10. FIG. 13 illustrates a bone 1300 and a defect 1302. Membrane 10 may include perforations 18, reinforcement binder 12, and/or other components. Membrane 10 may be placed across, over, and/or around defect 1302 and fastened in place at defect 1302 by screws, tacks, pins, and/or other fasteners 1304. Membrane 10 may facilitate bone regeneration 1306 as described herein.

Figure 14:
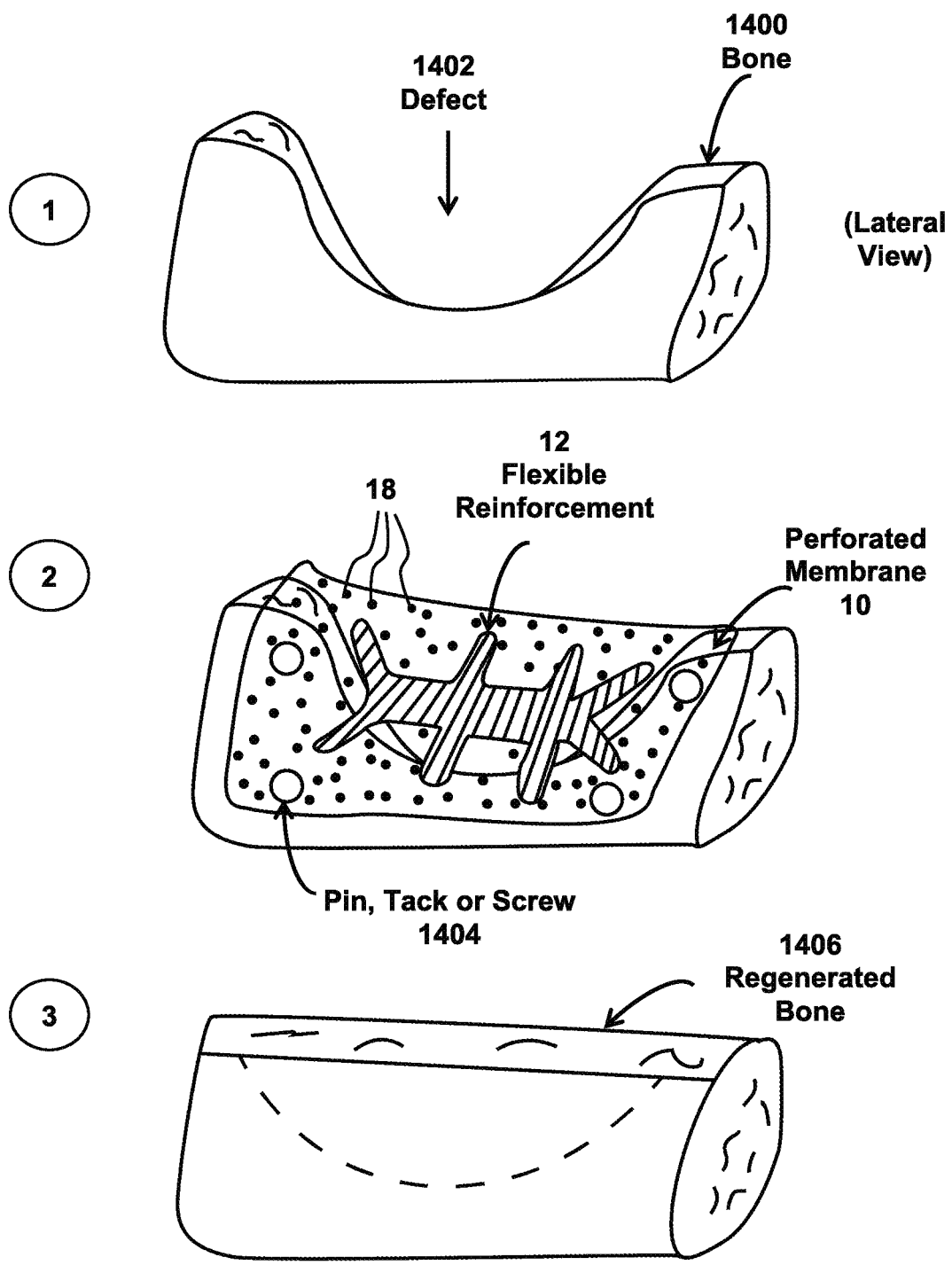
FIG. 14 illustrates treatment of a vertical defect with the membrane.

FIG. 14 illustrates treatment of a vertical defect with membrane 10. FIG. 14 illustrates a bone 1400 and a defect 1402. Membrane 10 may include perforations 18, reinforcement binder 12, and/or other components. Membrane 10 may be placed across, over, and/or around defect 1402 and fastened in place at defect 1402 by screws, tacks, pins, and/or other fasteners 1404. Membrane 10 may facilitate bone regeneration 1406 as described herein.

Figure 15:
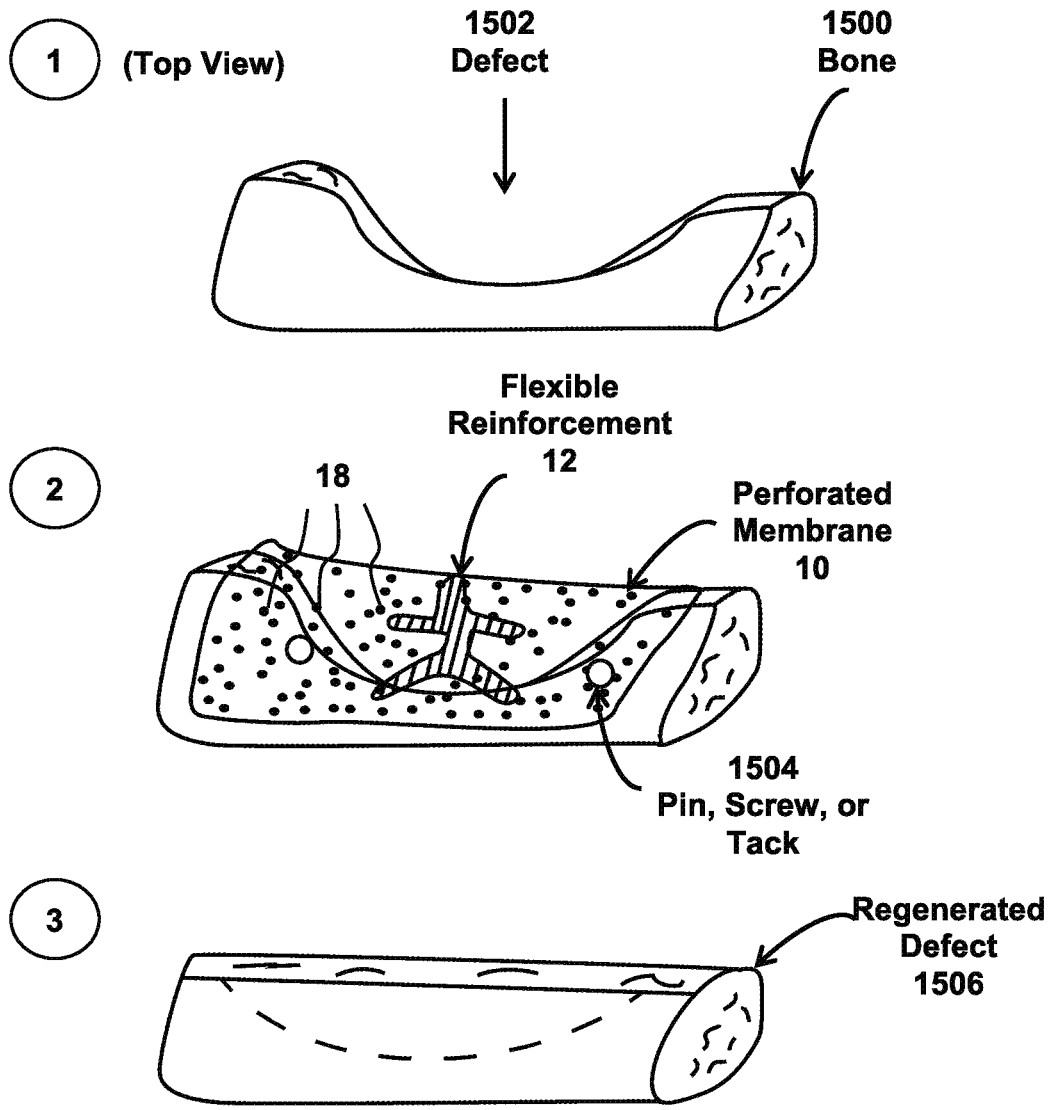
FIG. 15 illustrates treatment of a horizontal defect with the membrane.

FIG. 15 illustrates treatment of a horizontal defect with membrane 10. FIG. 15 illustrates a bone 1500 and a defect 1502. Membrane 10 may include perforations 18, reinforcement binder 12, and/or other components. Membrane 10 may be placed across, over, and/or around defect 1502 and fastened in place at defect 1502 by screws, tacks, pins, and/or other fasteners 1504. Membrane 10 may facilitate bone regeneration 1506 as described herein.

Figure 16:
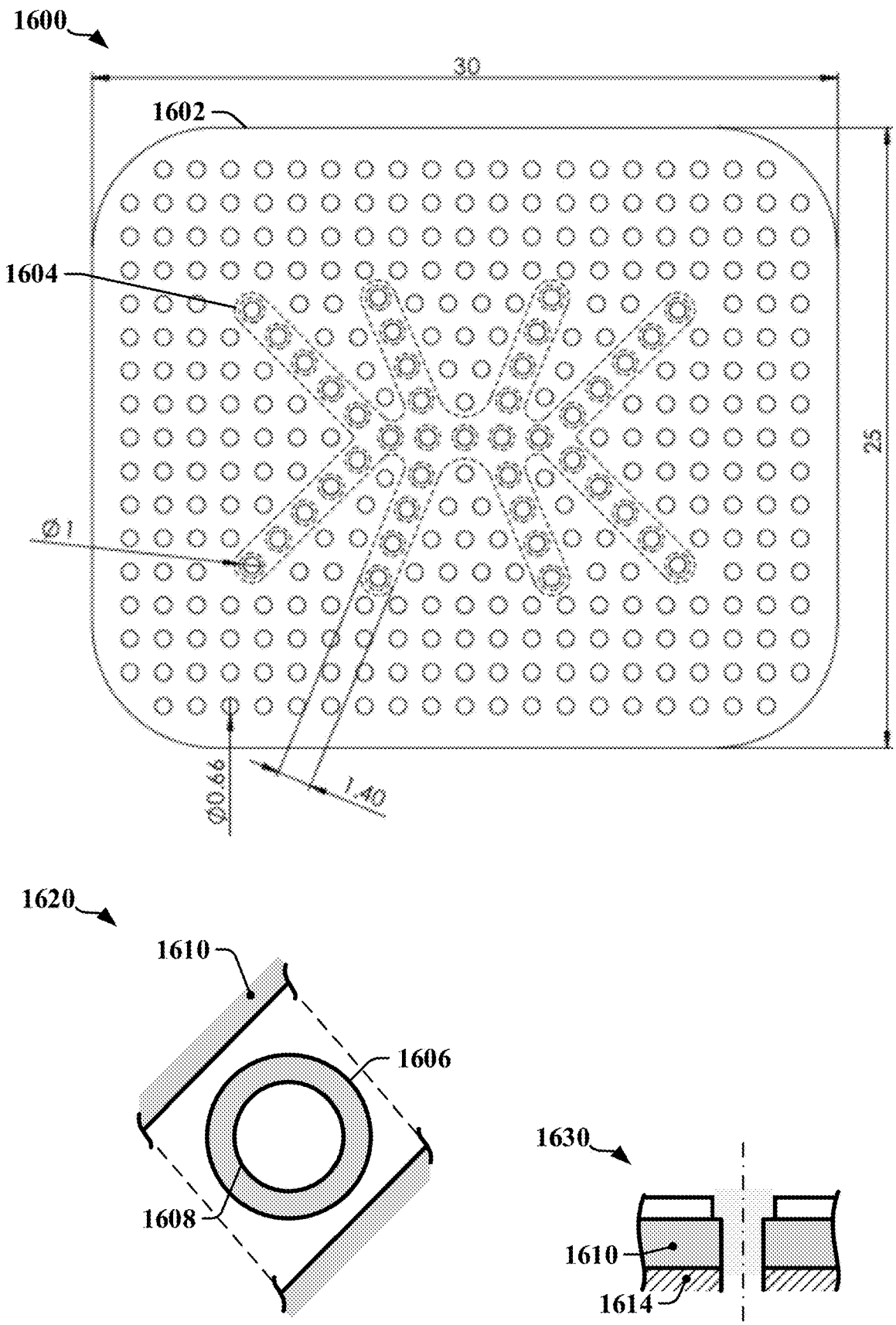
FIG. 16 illustrates a device that comprises a membrane 1602 and a reinforcement binder in accordance with certain aspects disclosed herein.

FIG. 16 illustrates certain additional aspects related to a device 1600 that comprises a membrane 1602 and a reinforcement binder 1604. The device 1600, membrane 1602 and/or reinforcement binder 1604 may share certain characteristics with the device, membrane 10 and binder 30 illustrated in FIG. 1. In some examples, the membrane 1602 may be configured to guide bone and tissue regeneration for a bone defect. In some examples, the membrane 1602 may be suitable for guided bone regeneration, guided tissue regeneration, and/or other therapies. The membrane 1602 may form a barrier used for guiding bone and tissue regeneration for dental and/or other purposes. The membrane 1602 may be used in oral surgery, maxillofacial surgery, craniofacial surgery, to treat periodontal diseases, for dental implants, to treat orbital floor bone defects, and/or for other applications. The membrane 1602 may be configured to maintain space for bone regeneration, to prevent connective tissue fibers from growing into the bone tissue, to immobilize bone, to exclude stimuli, which may hinder bone generation, and/or for other purposes. In some instances, the membrane 1602 may function as a barrier that is applicable in alveolar ridge defect replacements and/or for other defects that the membrane 1602 can be sized to cover. The membrane 1602 may facilitate reducing and/or eliminating injuries, and/or facilitate a more efficient bone and tissue regeneration process compared to previously known techniques. The membrane 1602 may include perforations 1608 located at various distances from each other throughout the membrane 1602.

The perforations 1608 in the membrane 1602 can positively affect bone regeneration. The device 1600, when in use, may comprise a perforated membrane 1602 that has a discontinuous surface located adjacent to the site of the desired bone and tissue regeneration and/or in contact with at least a portion of bone and tissue surrounding the site of the desired bone and tissue regeneration. The discontinuous surface may be formed with openings in the surface corresponding to the perforations 1608. The discontinuous surface may have a texture that is uneven, bumpy and/or rough, and the texture may result from a distribution of pores formed at the surface. The presence of perforations 1608 and/or surface pores causes the device 1600 to present the discontinuous surface at the site of the desired bone and tissue regeneration.

In one example, the size of each perforation 1608 (or the average size of the perforations 1608) on the surface of the membrane 1602 at the site of the desired bone and tissue regeneration is greater than the size of each pore (or the average size of the pores) on the surface of the membrane 1602 at the site of the desired bone and tissue regeneration. The positive effect on bone regeneration provided by the configuration of the discontinuous surface of the membrane 1602 at the site of the desired bone and tissue regeneration may be further enhanced through the use of various biological growth factors. Membranes with perforations have been shown to better facilitate bone regeneration than membranes without perforations. The perforated membrane design can also make the membrane 1602 easier to handle, fixate, and/or shape during application because the surgeon may more readily visualize, for example, pilot holes made specifically for the purpose of securing membrane fixation screws, pins or tacks.

In various examples, the membrane 1602 may include ePTFE having pores that range in size from 30 microns to 500 microns formed therein. In one example, the membrane 1602 includes pores having a maximum cross-sectional size that is less than 500 microns. The pores may be configured to promote ingrowth of bone regenerating cells into the first layer. The membrane 1602 may have perforations 1608 that facilitate communication between a patient's periosteum and growth factors used with GBR, where the growth factors may include RhPDGF, RhBMP, and/or other growth factors. The perforations 1608 may also facilitate communication between the periosteum and undifferentiated stem cells, especially in the presence of simulative growth factors. Application of a non-perforated collagen (for example) membrane may reduce the regenerative potential of PDGF. If a surgeon (and/or other users) utilizes ground autogenous bone for bone generation, which makes the application of a membrane necessary, the "permeability" of a perforated membrane 1602 may make the development of a connection with the periosteal membrane possible using the PDGF technique.

Similarly, the membrane 1602 may be used with RhBMP. Using the membrane 1602 with RhBMP may allow a surgeon (and/or other users) to avoid using a titanium net/mesh (used for its permeability relative to a non-perforated membrane), for example. A titanium net/mesh may cause complications because it is sharp and difficult to handle. Such complications may include, for example, damaging the gum of a patient or difficult removal (taking as long as thirty minutes). Conversely, the membrane 1602 may be removable in a matter of a few minutes, which decreases the duration of surgery and the possible occurrences of complications.

The perforations 1608 may comprise co-axial through-holes having common dimensions through at least a first layer 1610 and second layer 1614 (see expanded view 1620 and cross-sectional view 1630). In some implementations, as described herein, perforations 1608 may be restricted to the second layer, with the first layer being continuous, and fabricated of lightweight polymer mesh, collagen or expanded PTFE, for example. The perforations 1608 may be configured to enhance ossification. In some implementations, the perforations 1608 may have a substantially circular shape. In some implementations, the perforations 1608 may have a substantially circular cross section. In some implementations, the perforations 1608 may have a form factor other than circular. For example, perforations may be substantially shaped as a square, a rectangle, a triangle, a diamond, an oval, a pentagon, a hexagon, an octagon, a free form shape, and/or other shapes. In some implementations, one or more of the perforations 1608 may include perforations having a substantially circular cross section having a diameter of about 0.1 mm or larger. In some implementations, one or more of the perforations 1608 may include perforations with a substantially circular cross section having a diameter of about 0.5 mm to about 1.0 mm. In some implementations, one or more the perforations 1608 may include perforations with a substantially circular cross section having a diameter of up to about 3.0 mm. In some implementations, the shape and/or size of the perforations 1608 may vary across the membrane 1602. For example, the perforations 1608 may be smaller near reinforcement binder 1604 and larger near the edges of the membrane 1602.

The shapes and/or dimensions of the perforations 1608 described above are not intended to be limiting. The perforations 1608 may have any size and/or shape that allows them to function as described herein. In some implementations, a size, a shape, a density, a spacing, and/or other characteristics of the perforations 1608 may be determined based on one or more of a material that forms the membrane 1602, a thickness of the membrane 1602, a size (e.g., length and width) of the membrane 1602, a shape and/or size of the reinforcement binder 1604, an intended use for the membrane 1602, and/or other factors.

In some implementations, the membrane 1602 may be configured such that the perforations 1608 may be formed at manufacture, formed by a user (e.g., a surgeon, a doctor, a nurse, and/or other clinicians), and/or formed at other times. In some implementations, the perforations 1608 may be formed during an individual procedure according to the needs of the patient and/or the bone defect. For example, a user may use a sharp tool to perforate or otherwise pierce the perforations 1608, a tool associated with the membrane 1602, and or other devices to make the perforations 1608. In such implementations, the number and/or the spacing of the perforations 1608 may be determined by the user. In such implementations, the shape of the perforations 1608 may depend on the tool used to make the perforations 1608.

In some implementations, one or more of the perforations 1608 in the membrane 1602 may be configured to receive fasteners 1616 configured to hold the membrane 1602 in place at the bone defect. Other perforations 1608 in the membrane 1602 may play no role in fastening the membrane 1602 at the bone defect at the time of installation. Certain perforations 1608 that are used for fastening or other such purposes may have a different size, shape, and/or density relative to other perforations. The perforations 1608 that are used for fastening may be configured to receive fasteners 1616 that can be pins (e.g., Titanium Master Pins manufactured by the Meisinger corporation), titanium tacks, screws (e.g., manufactured by Pro-Fix, Osteogenics, etc.), and/or other fastening devices.

The reinforcement binder 1604 may comprise multiple elongated members extending from a junction. In some implementations, the reinforcement binder 1604 may be formed between layers of the membrane 1602. In the illustrated example, the reinforcement binder 1604 may be provided above or below two or more layers 1610, 164 of the membrane 1602. In some implementations, the reinforcement binder 1604 may be formed from titanium, stainless steel, platinum, ceramics, composites, carbon fiber materials, customized micro and/or nano material based materials, coated (e.g., with a non-toxic coating) materials, and/or other materials. The reinforcement binder 1604 may be bendable and may include elongate members such that the reinforcement binder 1604 may be formed in a desired shape (e.g. at manufacture), and/or may be bent, deformed, and/or reformed by a user to obtain the desired shape prior to placement about the bone defect such that the formed shape is maintained upon placement. For example, one or more portions and/or all of the reinforcement binder 1604 may be bent, twisted, and/or stretched as necessary to obtain the desired shape. In some implementations, the reinforcement binder 1604 may be sufficiently thin to promote malleability and/or flexibility. For example, a thin piece of titanium may be easily bent by a user.

In some instances, the reinforcement binder 1604 comprises a titanium frame. The titanium frame may have one or more holes 1606 that are configured to align concentrically with corresponding perforations 1608 in the membrane

1602. The holes 1606 in the titanium frame may have a greater diameter than the perforations 1608 through the layers 1610, 1614 of the membrane 1602. The different diameters of the holes 1606 in the titanium frame and corresponding perforations 1608 in the membrane 1602 may improve manufacturability and ease of use of the device 1600, including when one or more layers 1610, 1614 of the membrane 1602 comprise PTFE. In some instances, the difference in diameters of the holes 1606 in the titanium frame and corresponding perforations 1608 in the membrane 1602 may be configured to accommodate the structure or profile of a fastener 1616. In some instances, the holes 1606 in the titanium frame may be beveled and/or provide a countersunk profile to accommodate certain types of a fastener 1616.

According to certain aspects, at least one perforation 1608 extends through all layers of the membrane 1602 and the reinforcement binder 1604 is configured to be placed over the bone defect and further configured to couple with surrounding bone. The reinforcement binder 1604 may include multiple elongated members extending from a junction, the elongated members including a first elongated member having a free end that extends away from the junction with a predrilled hole formed in the first elongated member. The predrilled hole may be configured to receive a fastener 1616 that passes through the first layer of the membrane 1602 and the second layer of the membrane 1602 and holds the membrane 1602 in place at the site of a bone defect.

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

The invention claimed is:

1. A membrane configured to guide bone and tissue regeneration for a bone defect, the membrane comprising:
   a first layer made of expanded polytetrafluoroethylene (PTFE) configured to contact bone and including first pores in a size range of 30 micrometers to 1000 micrometers;
   a second layer made of an unsintered, substantially unexpanded PTFE having a denser structure compared to the first layer and having second pores formed therein that provide a limited porosity that allows for passage of ions and other small molecules necessary for cellular nourishment and waste transport, wherein pore channels provided by the second pores formed in the second layer have a nominal pore channel size of less than 5 micrometers, and wherein the second layer is fixedly coupled to the first layer; and
   a reinforcement binder configured to be placed over the bone defect and to couple with surrounding bone, the reinforcement binder comprising multiple elongated members extending from a junction, the elongated members including a first elongated member having a free end that extends away from the junction with a predrilled hole formed therein, the predrilled hole being configured to receive a fastener that passes through at least one of the first or second layer of the membrane and to hold the membrane in place at the bone defect,
   wherein the membrane is configured to be spread over the bone defect,
   wherein first perforations formed in the membrane during manufacture of the membrane or formed in the membrane by a user are provided across a surface of the membrane and extend through the membrane,
   wherein second perforations formed in the membrane during manufacture of the membrane or formed in the membrane by the user are configured to receive fasteners that are configured to fasten the membrane to an area of bone, thereby holding the membrane in place at the bone defect,
   wherein each of the first perforations comprise co-axial through-holes and extend through all layers of the membrane and have a substantially circular cross-section with a diameter of between 0.1 mm and 3.0 mm throughout all layers of the membrane, and
   wherein certain of the first perforations are located near the reinforcement binder and have smaller diameters than at least one of the first perforations that is located near an edge of the membrane.

2. The membrane of claim 1, wherein the first perforations have a diameter of about 0.5 mm to about 1.0 mm.

3. The membrane of claim 1, wherein the membrane has a thickness from about 0.125 mm to about 0.25 mm.

4. The membrane of claim 1, wherein the fasteners comprise pins, tacks, sutures or screws.

5. The membrane of claim 1, wherein the reinforcement binder is formed between the first layer and the second layer of the membrane.

6. The membrane of claim 1, wherein the first pores are formed during manufacture of the expanded PTFE used to make the first layer.

7. The membrane of claim 6, wherein each of the first pores is formed as a cavity in the expanded PTFE used to make the first layer.

8. The membrane of claim 1, wherein the second pores are formed during manufacture of the unsintered, substantially unexpanded PTFE used to make the second layer.

9. The membrane of claim 8, wherein each of the second pores is formed as a cavity in the unsintered, substantially unexpanded PTFE used to make the second layer.

10. The membrane of claim 1, wherein the pore channels provided by the second pores have a nominal pore channel size of less than 2 micrometers.

11. The membrane of claim 1, wherein the pore channels provided by the second pores have a nominal pore channel size of less than 0.5 micrometers.

12. The membrane of claim 1, wherein the pore channels provided by the second pores have a nominal pore channel size of less than 0.2 micrometers.

13. The membrane of claim 1, wherein the first pores have a size that is less than 500 micrometers.

14. The membrane of claim 1, wherein the second layer is fixedly coupled to the first layer using an adhesive layer.

\* \* \* \* \*